(12) United States Patent
Musuvathy et al.

(10) Patent No.: US 9,474,582 B2
(45) Date of Patent: Oct. 25, 2016

(54) PERSONALIZED ORTHOPEDIC IMPLANT CAD MODEL GENERATION

(75) Inventors: Suraj Ravi Musuvathy, Lawrence, NJ (US); Ruirui Jiang, Stony Brook, NY (US); Sergei Azernikov, Irvine, CA (US); Gang Li, Princeton, NJ (US); Tong Fang, Morganville, NJ (US)

(73) Assignee: Siemens Aktiengesellschaft, München (DE)

( * ) Notice: Subject to any disclaimer, the term of this patent is extended or adjusted under 35 U.S.C. 154(b) by 915 days.

(21) Appl. No.: 13/817,272

(22) PCT Filed: Aug. 16, 2011

(86) PCT No.: PCT/US2011/047838
§ 371 (c)(1),
(2), (4) Date: Mar. 12, 2015

(87) PCT Pub. No.: WO2012/027150
PCT Pub. Date: Mar. 1, 2012

(65) Prior Publication Data
US 2015/0230874 A1    Aug. 20, 2015

Related U.S. Application Data

(60) Provisional application No. 61/376,733, filed on Aug. 25, 2010.

(51) Int. Cl.
*G05D 1/00* (2006.01)
*A61B 19/00* (2006.01)
(Continued)

(52) U.S. Cl.
CPC ........... *A61B 19/50* (2013.01); *G06F 19/3437* (2013.01); *G06T 17/20* (2013.01); *G06T 17/30* (2013.01); *A61B 2019/508* (2013.01)

(58) Field of Classification Search
CPC ................ A61F 2/30942; A61F 2002/30952; A61F 2002/2835; A61F 2/30756; A61F 2002/30062; A61F 2002/30677; A61F 2002/30943; A61F 2002/30948; A61F 2002/30962; A61F 2210/0004; A61F 2310/00293; A61F 2/28; G06T 17/20; A61B 17/15; A61B 17/158; A61B 17/1666; A61B 17/1668; A61B 17/1675; A61B 17/1739; A61B 2017/568; A61B 2019/5255; A61B 6/505; A61B 17/151; A61B 17/152; A61B 17/154; A61B 17/16; A61B 17/164
USPC ............................................................ 703/1
See application file for complete search history.

(56) References Cited

U.S. PATENT DOCUMENTS 7,289,121 B1 * 10/2007 Balakrishnan ........ G06T 11/203
345/419
2002/0007294 A1    1/2002 Bradbury
(Continued)

FOREIGN PATENT DOCUMENTS

WO    WO 0110339 A2    2/2001

OTHER PUBLICATIONS

Jiang_2009.pdf T. Jiang, F. Lin, S.I. Kaltman, W. Sun Anatomical modeling and rapid prototyping assisted surgical reconstruction Proceedings of the Eleventh Solid Freeform Fabrication Symposium, University of Texas Austin (2009), pp. 555-564.*
Hosni_2002.pdf Yasser A. Hosni, Ola L.A. Harrysson, Design and Manufacturing of Customized Implants, IERC 2002, Orlando, Florida, USA, May 19-21, 2002.*
(Continued)

*Primary Examiner* — Kamini S Shah
*Assistant Examiner* — Scott S Cook

(57) ABSTRACT

A computer assisted method creates accurate CAD/CAM models of custom orthopedic implants is provided. Information about bone geometry is acquired through medical imaging such as CT image scans. The desired bone surface region is extracted as a polygonal mesh after processing the 3D images. A smooth and accurate B-Spline surface is fitted to the polygonal mesh that is thickened to a solid CAD model. A patient-specific customized implant is manufactured from the obtained CAD model. The patient-specific customized implant is implanted in a patient by a surgeon in an operating room. A processor based system to generate a CAD/CAM file of the patient-specific customized implant and a manufacturing system enabled to manufacture the implant from the CAD/CAM file are also disclosed.

18 Claims, 21 Drawing Sheets

(51) Int. Cl.
*G06F 19/00* (2011.01)
*G06T 17/20* (2006.01)
*G06T 17/30* (2006.01)

(56) References Cited

U.S. PATENT DOCUMENTS

| | | | | |
|---|---|---|---|---|
| 2004/0113910 | A1* | 6/2004 | Tsai | G06T 17/30 345/420 |
| 2006/0094951 | A1* | 5/2006 | Dean | A61F 2/30942 600/407 |
| 2007/0118243 | A1* | 5/2007 | Schroeder | A61B 17/8061 700/118 |
| 2009/0254367 | A1* | 10/2009 | Belcher | G06Q 50/22 705/2 |
| 2011/0029093 | A1* | 2/2011 | Bojarski | A61F 2/30942 623/20.35 |

OTHER PUBLICATIONS

Laug_2003.pdf Interpolating and meshing 3D surface grids, 2003 John Wiley & Sons, Ltd.*

Bajaj_1995.pdf "Splines and Geometric Modeling" (1995). Computer Science Technical Reports. Paper 1230. http://docs.lib.purdue.edu/cstech/1230.*

Bhagalia_2008.pdf Analysis and Strategies to Enhance Intensity-Based Image Registration, Dissertation, University of Michigan 2008.*

Dierckx_1993 (Curve and Surface Fitting with Splines, Oxford University Press, 1993).*

Schreiner_2006 (High-Quality Extraction of Isosurfaces from Regular and Irregular Grids, IEEE transactions on Visualization and Computer Graphics, vol. 12, No. 5, Sep./Oct. 2006).*

Ming, L., Least Squares Approximation, Intergraph Mar. 1997.*

\* cited by examiner

PERSONALIZED ORTHOPEDIC IMPLANT CAD MODEL GENERATION

STATEMENT OF RELATED CASES

This case claims priority to and the benefit of U.S. Provisional Patent Application Ser. No. 61/376,733, filed Aug. 25, 2010.

TECHNICAL FIELD

The present invention relates to systems and methods for generating custom or patient specific orthopedic implants.

BACKGROUND

Orthopedic implants are used to replace parts of patients' bones to treat disorders such as arthritis and injuries caused by accidents, stress, disease or other problems. Replacement surgery involves removing part of the bone that is then replaced with an implant. This procedure is typically called resurfacing. Currently, implants are available in standard sizes and require removal of a fairly large amount of bone during resurfacing.

Since standard sizes are used, this approach may lead to the removal of a large amount of healthy bone, which is undesirable. However, the generation of personalized implants is technically difficult. Typically, anatomical entities are highly curved. Thus, anatomical entities present technical challenges due to the highly curved free from nature of surface geometry.

Accordingly, new and improved approaches to creating implants for use in replacement surgery are required.

SUMMARY OF THE INVENTION

One aspect of the present invention provides methods and systems to create customized implants that conform closely to a patient's bone in order to improve comfort and performance and also, to reduce resurfacing, thereby retaining a larger amount of healthy bone.

In accordance with an aspect of the present invention, a computer assisted method and system for creating accurate CAD models of custom orthopedic implants, is provided. Information about the bone geometry is acquired through CT image scans. The desired bone surface region is extracted as a polygonal mesh after processing the 3D images. A smooth and accurate B-Spline surface is fit to the polygonal mesh that is then thickened to a solid CAD model. A patient-specific customized implant can be manufactured from the obtained CAD model.

The approach of the present invention is demonstrated with an example of creating distal femur implants for partial or total knee replacement surgeries. The present invention is applicable to other implant procedures as well.

Accurate custom implants made in accordance with the present invention improve patient comfort and performance by better fitting a patient. The custom designed implants of the present invention also generally reduce the amount of bone resurfacing thereby allowing retention of a larger amount of healthy bone.

A complete workflow of creating solid models from medical images in a unified manner is provided. Typically, image acquisition and processing, conversion of meshes to B-Spline surfaces (reverse engineering) and creation of solid models from surfaces (CAD modeling) are available in different independent software systems. An implementation of the proposed workflow provided herein demonstrates the feasibility of creating a unified system to perform all required functions. A product for creating custom implants based on such a unified system will have better market potential by enabling faster turnaround times with improved quality. Anatomical entities present technical challenges due to highly curved freeform nature of surface geometry.

In accordance with one aspect of the present invention, a method of making an implant from an image of a bone is provided. A processor receives image data of the image of the bone, segments a desired bone from the image data to create a segmentation of the desired bone, creates a polygonal mesh from the segmentation of the desired bone, extracts a part of the polygonal mesh corresponding to an implant region and parameterizes the part of the polygonal mesh so that every vertex therein is associated with two parameter values. The processor also resamples the polygonal mesh to generate a grid of 3D points regularly spaced in parametric domain and fits a B-spline surface to the grid using a least squares process, which can be weights. The processor can also smooth the surface.

A solid CAD model can be created from the B-spline surface. Assembly features can be added to the CAD model. The assembly features can be a pin and screw thread. The implant can be manufactured using a CAM system. The polygonal mesh can be created using a Marching Cubes process or an Afront process or any other applicable process.

In accordance with a further aspect of the present invention, the least squares process involves minimizing $$F_{smooth}(Q) = \sum_{k=0}^{r} w_k^2 \|S(u_k, v_k) - P_k\|^2 +$$
$$\lambda \sum_{k=0}^{r} (\|S_{uu}(u_k, v_k)\|^2 + \|S_{uv}(u_k, v_k)\|^2 + \|S_{vv}(u_k, v_k)\|^2)$$

where $w_k$ is a weighting coefficient, $S(u, v)$ is a surface, $P_k$ are sample points, $\lambda$ is a smoothing parameter, and $S_{uu}$, $S_{uv}$ and $S_{vv}$ are the second derivatives of the surface $S(u, v)$.

In accordance with a further aspect of the present invention, a method of making a patient specific implant is provided. In accordance with this method, an image of a portion of a patient's bone is taken. A processor is used to select a portion of the image to form a selected part of the image and processes the selected part of the image to form a surface. The processor creates a CAD model from the surface. Then a CAM system is used to manufacture the patient specific implant based on the CAD model. The method also comprising implanting the patient specific implant in the patient. In accordance with another aspect of the present invention, the CAM system can manufacture the customized medical implant from a preformed implant.

A corresponding system to perform these methods with a processor is also contemplated and described herein.

DESCRIPTION

Aspects of the present invention provide systems and methods to create orthopedic implants exhibiting complicated geometry.

Figure 1:
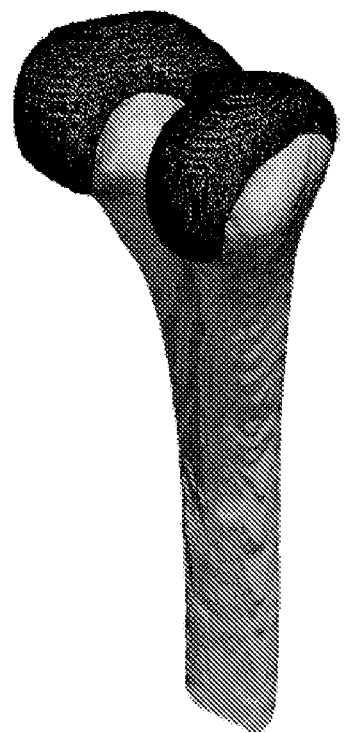
FIG. 1 illustrates a bone patient geometry.
Figure 2:
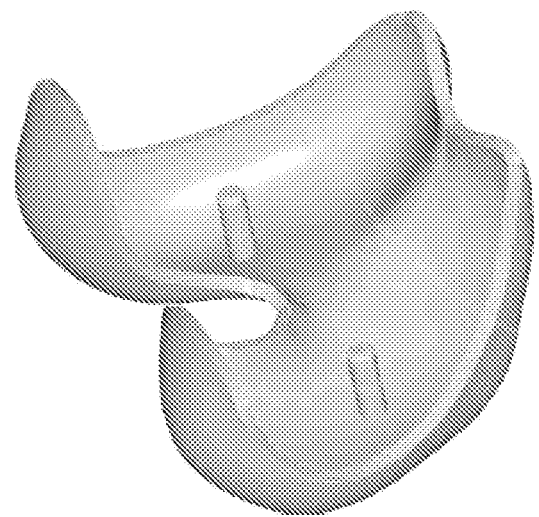
FIG. 2 illustrates a solid B-Spline of an customized implant to replace the distal femur bone region of a knee joint created in accordance with various aspects of the present invention.

FIG. 2 shows a solid B-Spline based model of a customized implant to replace the distal femur bone region of a knee joint shown in FIG. 1. The solid model has been created using the approach presented herein as an aspect of the present invention.

B-Splines are used in accordance with an aspect of the present invention. B-Splines are smooth piecewise polynomial functions. They are well suited for representations of freeform geometry such as the surfaces of anatomical objects. Further, B-Spline based solid CAD models are well known and are compatible with other CAD modeling systems and CAM systems for manufacturing. A CAD file that is enabled to be received by a manufacturing machine and used to produce a part such as an implant is called a CAM file. The solid implant models created using the approach presented in this paper may be enhanced or modified by other CAD systems and used for manufacturing using standard or specialized CAM systems.

In accordance with one embodiment of the present invention, the approach begins with the acquisition of the image (e.g., CT scan) of a patient's bone. The desired bone is then segmented from the image and a polygonal mesh is created. Methods to create the polygonal mesh are known. Any of the known method can be used. For example, the Marching Cubes process or the Afront process can be used.

The Marching Cubes process is described in W. Lorensen and H. Cline, "Marching cubes: A high resolution 3d surface construction algorithm," in *Proceedings of the 14th annual conference on Computer graphics and interactive techniques*. ACM, 1987, p. 169, which is hereby incorporated by reference. The Marching Cubes process approximates an isosurface by subdividing a region of space into 3D array of rectangular cells.

The Afront process is described in J. Schreiner, C. Scheidegger, and C. Silva, "High-quality extraction of isosurfaces from regular and irregular grids," *IEEE Transactions on Visualization and Computer Graphics*, pp. 1205-1212, 2006. This reference is hereby incorporated by reference. The Afront process is an advancing front triangulation algorithm that makes use of a guidance field to determine triangle sizing that is adaptive to the curvature of the input surface.

Then preprocessing is performed on the mesh to improve its quality. Part of the mesh corresponding to the implant placement region is extracted. The mesh is parameterized to associate every vertex with two parameter values. A grid of 3D points regularly spaced in parametric domain is obtained by resampling the polygonal mesh. A smooth and accurate B-Spline surface is fit to the samples grid using least squares based iterative techniques. A solid CAD model is then created from the surface and assembly features are added. The CAD model can then be used to manufacture customized implants using CAM systems.

Figure 3:
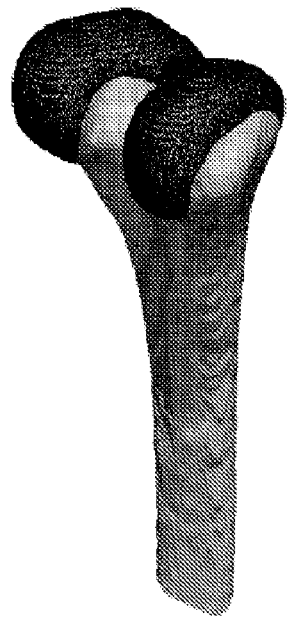
FIG. 3 illustrates a polygonal mesh representation of a femur bone in accordance with an aspect of the present invention.
Figure 4:
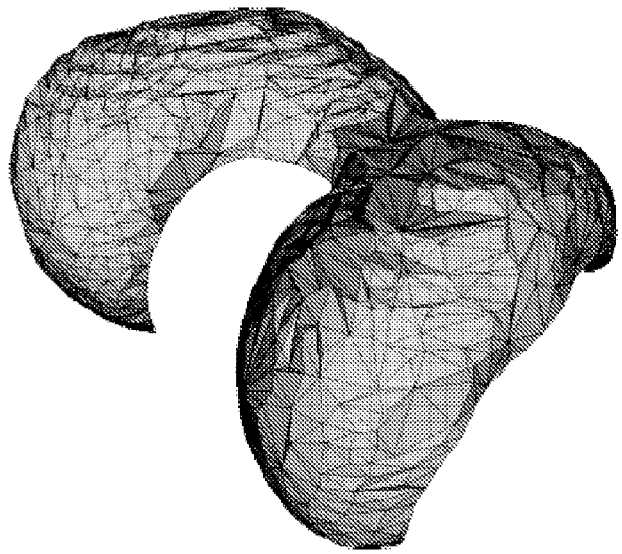
FIG. 4 shows the mesh corresponding to the region of interest extracted from the femur mesh in accordance with an aspect of the present invention.
Figure 5:
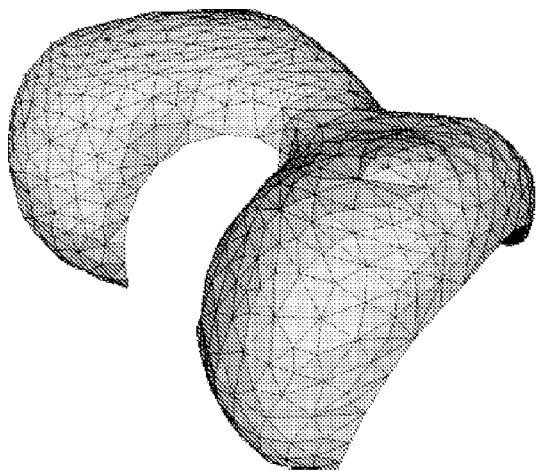
FIG. 5 illustrates further processing of the mesh to improve the triangulation quality in accordance with an aspect of the present invention.
Figure 6:
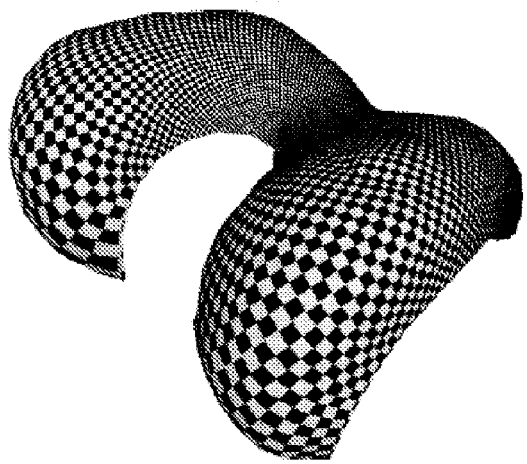
FIG. 6 illustrates the application of a checkerboard texture to the mesh using the computed parameter values at the vertices in accordance with an aspect of the present invention.
Figure 7:
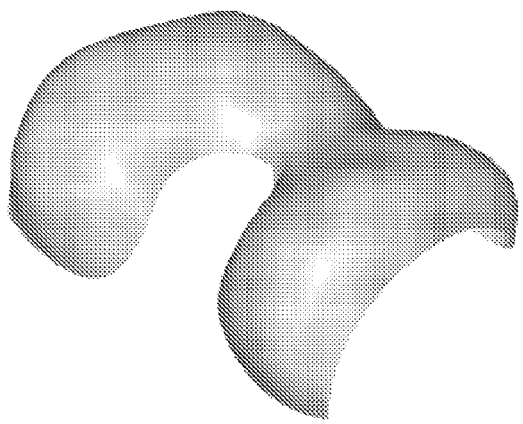
FIG. 7 shows a B-Spline surface fit to a regular grid of samples computed from the parameterized mesh in accordance with an aspect of the present invention.
Figure 8:
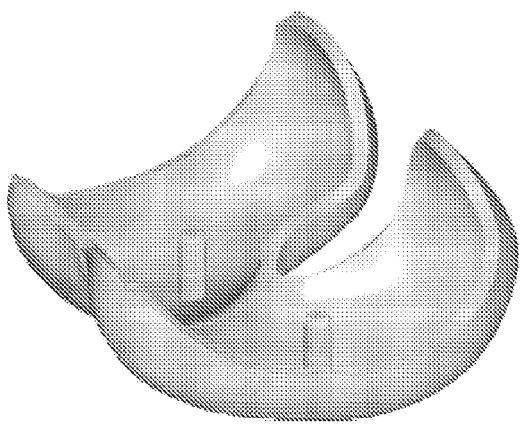
FIG. 8 shows a solid CAD model created from the B-Spline surface along with two pins added to insert the implant into the patient's femur bone in accordance with aspects of the present invention.

FIG. 3 illustrates a proposed approach for designing custom distal femur implants for knee joint replacements. The distal femur surface has two finger like extensions called condyles that are highly curved joined together by a central region called patellar surface. The outer boundary of the surface is also highly curved with concave regions. FIG. 3 shows a polygonal mesh representation of a femur bone computed from a CT scan. The region of interest where the implant is to be placed in the patient is also shown. FIG. 4 shows the mesh corresponding to the region of interest extracted from the femur mesh. This mesh is further processed to improve the triangulation quality as shown in FIG. 5. This step is necessary to improve the mesh parameterization result. The mesh is then parameterized. FIG. 6 shows a checkerboard texture applied to the mesh using the computed parameter values at the vertices. FIG. 7 shows a B-Spline surface fit to a regular grid of samples computed from the parameterized mesh. FIG. 8 shows a solid CAD model created from the B-Spline surface along with two pins added to insert the implant into the patient's femur bone.

BACKGROUND

This section presents a mathematical overview of surface parameterization, B-Spline surface representation and least squares based B-Spline surface approximation techniques.

A. Surface Parameterization

Recently a great number of 3D models are available and can be easily processed to triangle meshes. However, triangle mesh representation of free-form surfaces, although flexible, suffers from its high dimensional complexity (three coordinates per vertex) in a recognition point of view, and therefore the hardness of manipulation. Surface parameterization, as a technology to construct a mapping between the meshes and some parameter domain, therefore to reduce the 3D problems to 2D ones, is well studied and discussed.

Surface parameterization calculates specific kinds of mapping from surface itself to some parameter domain, e.g., the 2D plane. Surveys like provided in M. S. Floater and K. Hormann, "Surface parameterization: a tutorial and survey," in *In Advances in Multiresolution for Geometric Modelling*. Springer, 2005, pp. 157-186 and in A. Sheffer, E. Praun, and K. Rose, "Mesh parameterization methods and their applications," in *Foundations and Trends in Computer Graphics and Vision*. Now Publishers, 2006, pp. 105-171, give a comprehensive introduction to this topic.

Figure 9:
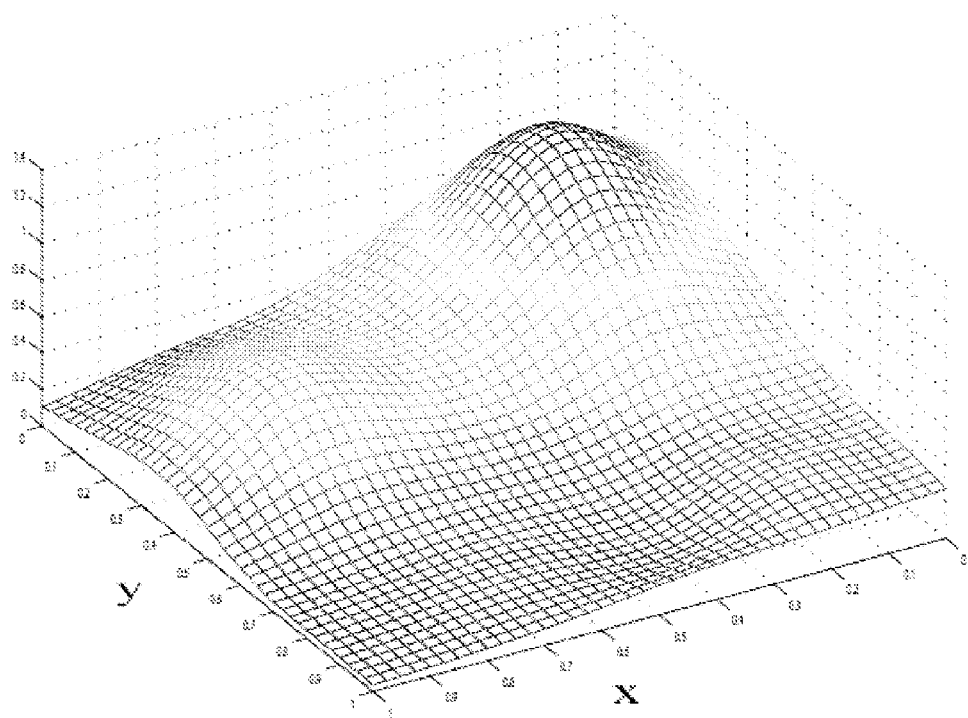
FIG. 9 illustrates a tensor product B-spline surface in accordance with aspects of the present invention.

In an application of reverse engineering, generally speaking, due to the spirit of tensor product B-spline, or NURBS, the parameter domain is a rectangle, or a polygon whose edges are all parallel to the axes. According to Equation (2), the spline surface can be acquired by first evaluating the spline curve in each of the x, y dimensions respectively, and then using tensor product structure to build the regular gird (see FIG. 9 for an example). It is highly desired that the iso-parametric lines are locally orthogonal to reduce the conversion error. To achieve this, Harmonic Mapping is employed to compute such a mapping.

Any mapping (u(x; y); v(x; y)) which satisfies the following two Laplace equations is called a harmonic mapping. A conformal mapping f satisfies the Cauchy-Riemann equations, which, with z=x+iy and w=u+iv, are $$\frac{\partial u}{\partial x} = \frac{\partial v}{\partial y}, \frac{\partial u}{\partial y} = \frac{\partial v}{\partial x}.$$

By differentiating one of these equations with respect to x and the other with respect to y one obtains the two Laplace equations:

$$\Delta u = 0, \Delta v = 0,$$

where $$\Delta = \frac{\partial^2}{\partial x^2} + \frac{\partial^2}{\partial y^2}$$

is the Laplace operator.

In the continuous domain, the parameterization problem can be formulated as follows: given a genus O surface $S \subset R^3$ with one boundary, compute a map f:

$$f: S \rightarrow R^2, f(\partial S) = \Gamma$$

where $\Gamma$ is a closed 2D curve.

There are infinitely many mapping from a surface to a 2D disk with fixed boundary. According to M. O. Carmo, *Differential Geometry of Curves and Surfaces*. Prentice Hall, 1976, the mapping from a surface embedded in $R^3$ to $R^2$ will cause distortions, either angle distortion, or area distortion, or both, unless the surface is developable. Here some method is sought to minimize the Dirichlet functional, or the string energy:

$$E(f) = \frac{1}{2} \int_S |\nabla f|^2.$$

This mapping is usually regarded as a harmonic map, which has a low angle distortion and is easy to compute.

The energy optimization is equivalent to solving the following PDE:

$$\Delta f = 0, \qquad (1)$$

where $\Delta$ is the Laplacian operator.

B. B-Spline Surfaces

B-Splines are piecewise polynomial functions. A tensor product B-Spline surface is given by:

$$S(u, v) = \sum_{i=0}^{m} \sum_{j=0}^{n} Q_{ij} N_{i,d_0,t_0}(u) N_{j,d_1,t_1}(v) \qquad (2)$$

where m and n are the number of control points in the u and v parametric directions. $N_{i,d_l,t_l}$, l=1, 2 . . . are B-Spline functions of degree $d_l$ with knot vector $t_l$. $Q_{ij} \in R^3$ are control points of the surface. See E. Cohen, R. Riesenfeld, and G. Elber, *Geometric modeling with splines: an introduction*. AK Peters Ltd, 2001 for further details about B-Splines and tensor product B-Spline surfaces, which is sufficiently known to one of ordinary skill.

C. Least Squares Surface Approximation and Variants

Given a regular grid of 3D points, a tensor product B-Spline surface can be fit to approximate the data grid such that the distance of the approximated surface and the data points is minimized. Least squares based surface approximation is widely used for this task as for instance described in E. Cohen, R. Riesenfeld, and G. Elber, *Geometric modeling with splines: an introduction*. AK Peters Ltd, 2001, and [7] L. Piegl and W. Tiller, *The NURBS book*. Springer Verlag, 1997.

The objective function to be minimized is given by $$F_{lsq}(Q) = \sum_{k=0}^{r} \|S(u_k, v_k) - P_k\|^2 \qquad (3)$$

where $P_k$ are the sample data points, $(u_k, v_k)$ are the parameter values of $P_k$ and $Q_{i,j}$ are the unknown variables. The degree is appropriately set; for e.g., cubic in both parametric directions.

$F_{lsq}$ is minimized by setting its partial derivatives with respect to $Q_{i,j}$ to zero and solving the resulting linear system for the unknown control points. The knot vectors are computed such that the every knot interval has at least one sample. This ensures that the resulting linear least squares matrix is positive definite as is known to one of ordinary skill and is also described in L. Piegl and W. Tiller, *The*

NURBS book. Springer Verlag, 1997 and C. De Boor, *A practical guide to splines*. Springer Verlag, 2001.

1) Weighted Least Squares:

The least squares technique may be enhanced by setting weights to samples to increase or decrease their influence for surface fitting. The least squares objective function may be modified as follows.

$$F_{wlsq}(Q) = \sum_{k=0}^{r} w_k^2 \|S(u_k, v_k) - P_k\|^2 \quad (4)$$

where $w_k$ is the assigned weight for $P_k$.

2) Smoothing Least Squares Splines:

The least squares techniques tend to introduce extraneous unwanted wiggles. These wiggles are small scale high curvature features. In order to obtain smooth surfaces, the least squares objective function may be modified to bound the magnitudes of second derivatives of the surface that in turn bounds the magnitude of the curvatures. The modified objective function is given by:

$$F_{smooth}(Q) = \sum_{k=0}^{r} w_k^2 \|S(u_k, v_k) - P_k\|^2 + \lambda \sum_{k=0}^{r} (\|S_{uu}(u_k, v_k)\|^2 + \|S_{uv}(u_k, v_k)\|^2 + \|S_{vv}(u_k, v_k)\|^2) \quad (5)$$

where $S_{uu}$, $S_{uv}$, $S_{vv}$ are the second derivatives of the surface $S(u,v)$. It is to be noted that the resulting system obtained after setting partial derivatives of $F_{smooth}$ to zero is still linear since the smoothing term is also a quadratic function of the control points. The smoothing parameter ($\lambda$) influences the quality of the approximation and must be chosen judiciously to obtain satisfactory results.

3) Constrained Least Squares Splines:

It is possible that some control points are fixed by external constraints. In this case the unknowns are the remaining control points and a surface approximation can be obtained by formulating a constrained least squares objective function. First rewrite the tensor product surface as follows.

$$S(u, v) = \sum_{l=0}^{M} Q_l N_l(u, v)$$

$M = mn, Q_l = Q_{i(l)j(l)}$ $N_l(u,v) = N_{i(l)}(u) N_{j(l)}(v) i(l) = [l/n], j(l) = l \mod n$ $Q_a$, $a \subset l=0 \ldots M$ are fixed control points. Let $L=l-a$. The constrained least squares objective function is given by equation (6):

$$F_{cons}(Q) = \sum_{k=0}^{r} \left\| \sum_{l=L_0}^{L_{|L|}} Q_l N_l(u_k, v_k) - \left(P_k - \sum_{\tilde{a}=a_0}^{a_{|a|}} Q_{\tilde{a}} N_{\tilde{a}}(u_k, v_k)\right) \right\|^2 \quad (6)$$

Workflow

In this section each step of the executed pipeline, from images to meshes, spline surfaces and finally CAD models in details is provided.

A. Image Acquisition and Mesh Generation

The high resolution CT image is first acquired. And some segmentation method is applied to extract the region of the bone from the background in each images. After that, a mesh generation method like Marching Cubes which is known to one of ordinary skill and is for instance described in W. Lorensen and H. Cline. "Marching cubes: A high resolution 3d surface construction algorithm," in *Proceedings of the 14th annual conference on Computer graphics and interactive techniques*. ACM. 1987. p. 169 gives the triangle mesh of the model.

B. Mesh Processing and Preparation

After the mesh of the entire model is obtained, it is further processed to get a decent one as the input of parameterization. First, the region of interest is highlighted and a cut a generated along the boundary between the region and other parts of the model. Then the mesh of highlighted region is extracted, with a special care of the quality of the cutting boundary.

Due to the consideration of numerical stability, smoothing or remeshing is performed (e.g. the algorithm as described in M. Botsch, M. Pauly, L. Kobbelt, P. Alliez, B. Levy, S. Bischoff, and C. Rossi, "Geometric modeling based on polygonal meshes," in *SIGGRAPH '07: ACM SIGGRAPH 2007 courses*. New York, N.Y., USA: ACM, 2007) if necessary. The resulting mesh should not contain very thin triangles, or floating triangles (ones two of whose edges are boundary edges).

C. Mesh Parameterization

Earlier herein, harmonic map was briefly introduced and why it is fitted to the present purpose. Next the implementation details are explained.

A triangle mesh M consists of a vertex set V, an edge set E, and a face F. Each vertex $v \in V$ is given its position in the Euclidean space $R^3$, i.e., $v = \{x_v, y_v, z_v\}$. The connection of vertices, or the topological information is encoded in the edge set and face set. Each edge e in E is connecting two vertices in V, i.e. $e_{ij} = [v_i, v_j]$. Similarly, three consecutive loop edges form a face in F, i.e., $f_{ijk} = [v_i, v_j, v_k]$. In the rest of this document, sometimes p is used instead of v to represent the vertices to avoid the confusion of similar symbols.

Using a finite element method, U. Pinkall and K. Polthier, "Computing discrete minimal surfaces and their conjugates," *Experimental Mathematics*, vol. 2, pp. 15-36, 1993 was able to find a solution to the discrete counterpart of Equation by defining the discrete Laplacian operator on the triangle mesh. It is known as the cotangent formula. The discrete Laplacian off at each vertex $v \in V$ in mesh M is:

$$\Delta f(v) = \sum_{\substack{v_j \in V \\ [v, v_j] \in E}} (\cot \alpha_{v, v_j} + \cot \beta_{v, v_j}).$$

Figure 10:
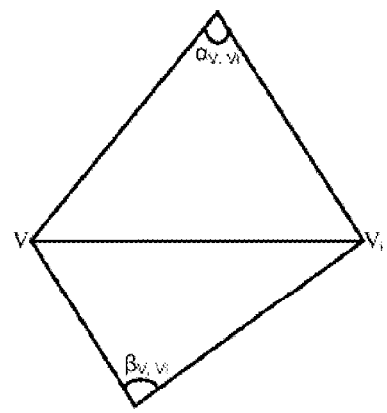
FIG. 10 illustrates coefficients of the discrete Laplacian operator in accordance with aspects of the present invention.

$\alpha_{v, v_j}$ and $\beta_{v, v_j}$ and are defined as shown in FIG. 10. When $[v, v_i]$ is a boundary edge, only one angle is considered.

Setting the Laplacian to 0 yields the solution to the harmonic map. Usually, such a process involves solving two linear systems, one for the x coordinate, and the other for the y coordinate. Program 1 shows in pseudo-code how to calculate the harmonic map from a disk-topology surface to a unit square. Note that the corner points, or the boundary condition need to be chosen carefully to reduce the distortion.

---
Program 1: Calculate the harmonic map from a disk to a unit square
---
Require: Triangle Mesh M with genus 0 and one boundary
Ensure: $\Delta f(v) = 0$ for $v \notin \partial M$, and $\partial f$ is a unit square
Segment $\partial M$ into four consecutive segments $\Gamma_i$ ($0 \leq i \leq 3$)
Mark all vertices unfixed
for each vertex p in $\Gamma_0$ do
  Set u(p) = 0, and mark p as fixed
end for
for each vertex p in $\Gamma_2$ do
  Set u(p) = 1, and mark p as fixed
end for
for each vertex p in M do
  if p is not fixed then
    Add $\Delta u(p) = 0$ to the linear system $\mathscr{U}$
  end if
end for
Solve linear system $\mathscr{U}$ to get u(p) for each vertex p
Mark all vertices unfixed
for each vertex p in $\Gamma_1$ do
  Set v(p) = 0, and mark p as fixed
end for
for each vertex p in $\Gamma_3$ do
  Set v(p) = 1, and mark p as fixed
end for
for each vertex p in M do
  if p is not fixed then
    Add $\Delta u(p) = 0$ to the linear system $\mathscr{V}$
  end if
end for
Solve linear system $\mathscr{V}$ to get v(p) for each vertex p
f(p) = (u(p), v(p))
---

The parameterization from a disk to other planar shapes is essentially the same. The only difference is to set different boundary conditions for each linear system.

D. Sample Grid Creation

The mesh is then resampled based on the parameterization result. For the square case, see Program 2 in pseudo-code for details. The template case is basically the same.

Sometimes the distortion along the boundary is much higher than other region. This can be solved by extracting a little more areas in the preprocessing step, then drop the boundary of the regular grid.

---
Program 2: Uniform sampling of the mesh to get a regular grid:
---
Require: Parameterized Triangle Mesh M with u(p) and v(p)
  for each vertex p, and sampling resolution RES
  for i ← 0 to RES do
    for j ← 0 to RES do
      In the parameter domain, find triangle $\Delta$ which contains planar point $p_{ij} = \left(\dfrac{i}{RES}, \dfrac{j}{RES}\right)$
      Calculate the Bari-centric coordinate of $p_{ij}$ with respect to $\Delta$
      Apply the coordinate interpolation in the 3D domain to get a sampling point $S_{ij}$
    end for
  end for
  Connect $S_{ij}$ to form a regular grid
---

E. B-Spline Surface Fitting

This section presents two methods for tensor product B-Spline surface fitting using least squares based techniques presented in an earlier section. First, an iterative method is presented for fitting a single B-Spline surface to a rectangular grid of samples with associated parameter values. Second, an algorithm is presented for fitting a multi-patch surface taking cross-boundary smoothness into consideration. Bi-cubic surfaces have been used for all results, and appear satisfactory. The iterative methods are variations of the approach presented in V. Weiss, L. Andor, G. Renner, and T. Varady, "Advanced surface fitting techniques," *Computer Aided Geometric Design*, vol. 19, no. I, pp. 19-42, 2002.

Figure 11:
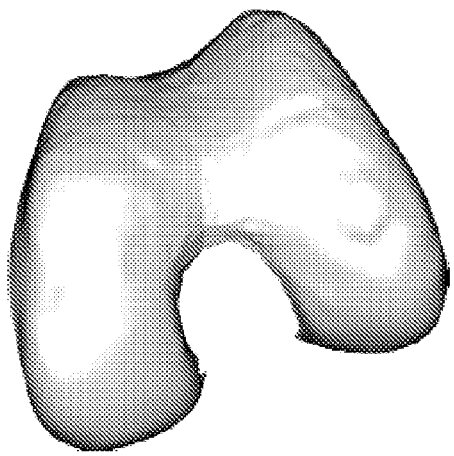
FIGS. 11, 12 and 13 illustrate a surface fit with plain least squares fitting in accordance with an aspect of the present invention.
Figure 12:
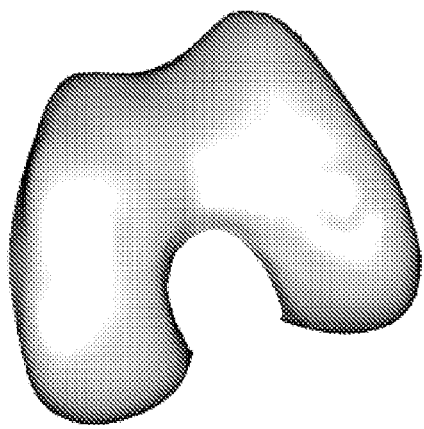
Figure 13:
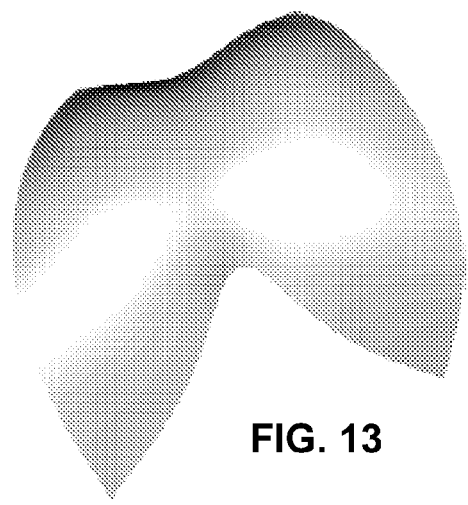

1) Single Patch Fitting: Given a rectangular grid of samples, an accurate and sufficiently smooth B-Spline surface is required. Least squares fitting without the smoothing term gives accurate surfaces but contain unwanted wiggles due to the nature of the fitting. The wiggles are not part of the original data set and cause additional problems when creating solid models. At the same time, a very large smoothing parameter will not give accurate surfaces. Therefore smoothing parameter values must be judiciously selected. FIG. 11 shows a surface fit with plain least squares fitting. This surface contains many unwanted small high curvature features. FIG. 13 shows a surface fit using a large smoothing parameter value. This surface is not a sufficiently accurate fit to the sample grid. FIG. 12 shows a surface obtained in accordance with a method provided in accordance with an aspect of the present invention. The surface is smooth as well as accurate. Comparison of the effects of smoothing parameter on least squares fitting is demonstrated in FIGS. 11-13. The control net size (53×53) and knot vectors for all three surfaces are the same. FIG. 11 No smoothing, $\lambda=0$; FIG. 12 Optimal smoothing, $\lambda=3.4*10^{-7}$; FIG. 13 Over smoothing, $\lambda=10^{-4}$.

Figure 14:
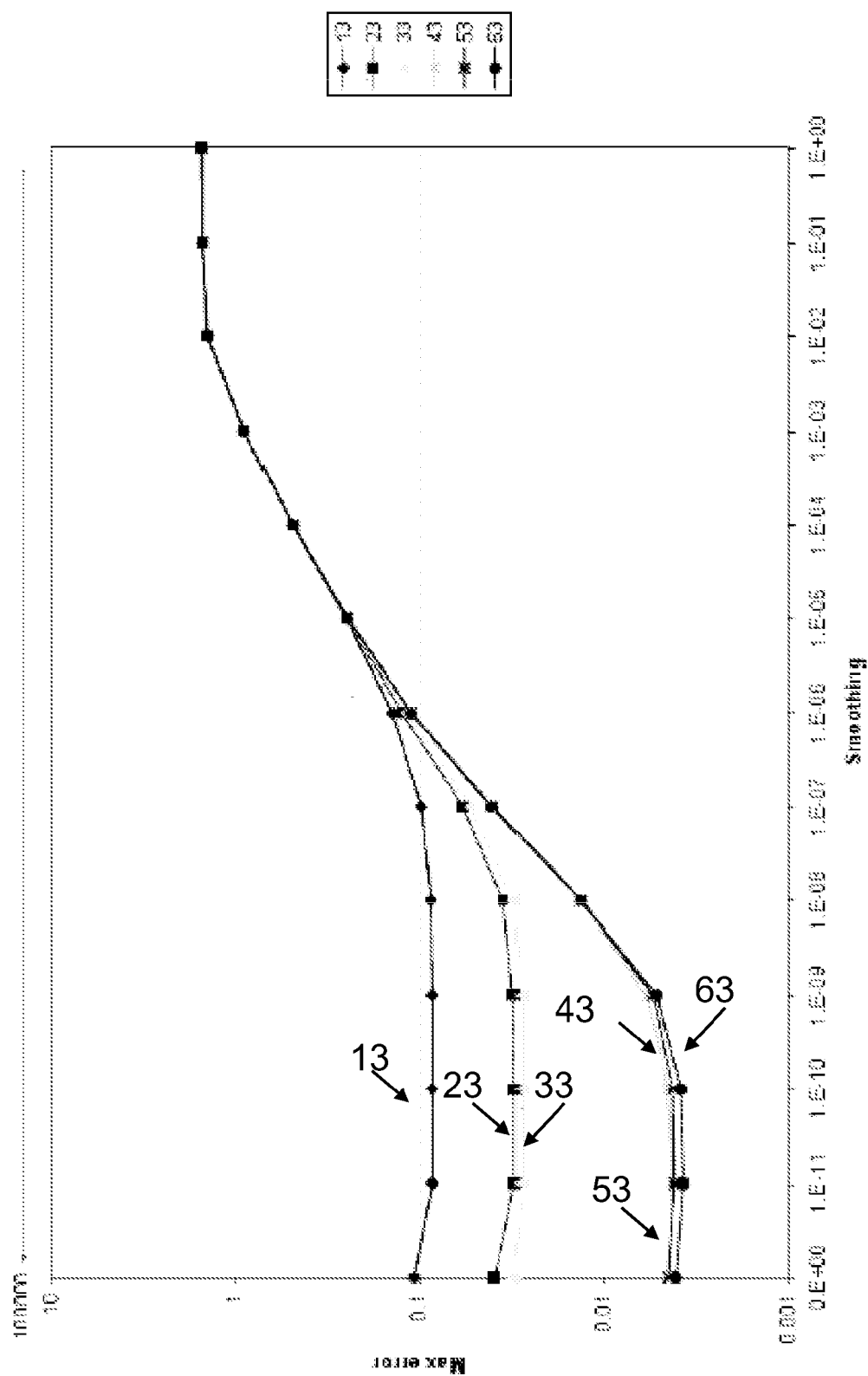
FIG. 14 illustrates a variation of the least squares residual error with increasing smoothing parameter value in accordance with an aspect of the present invention.
Figure 15:
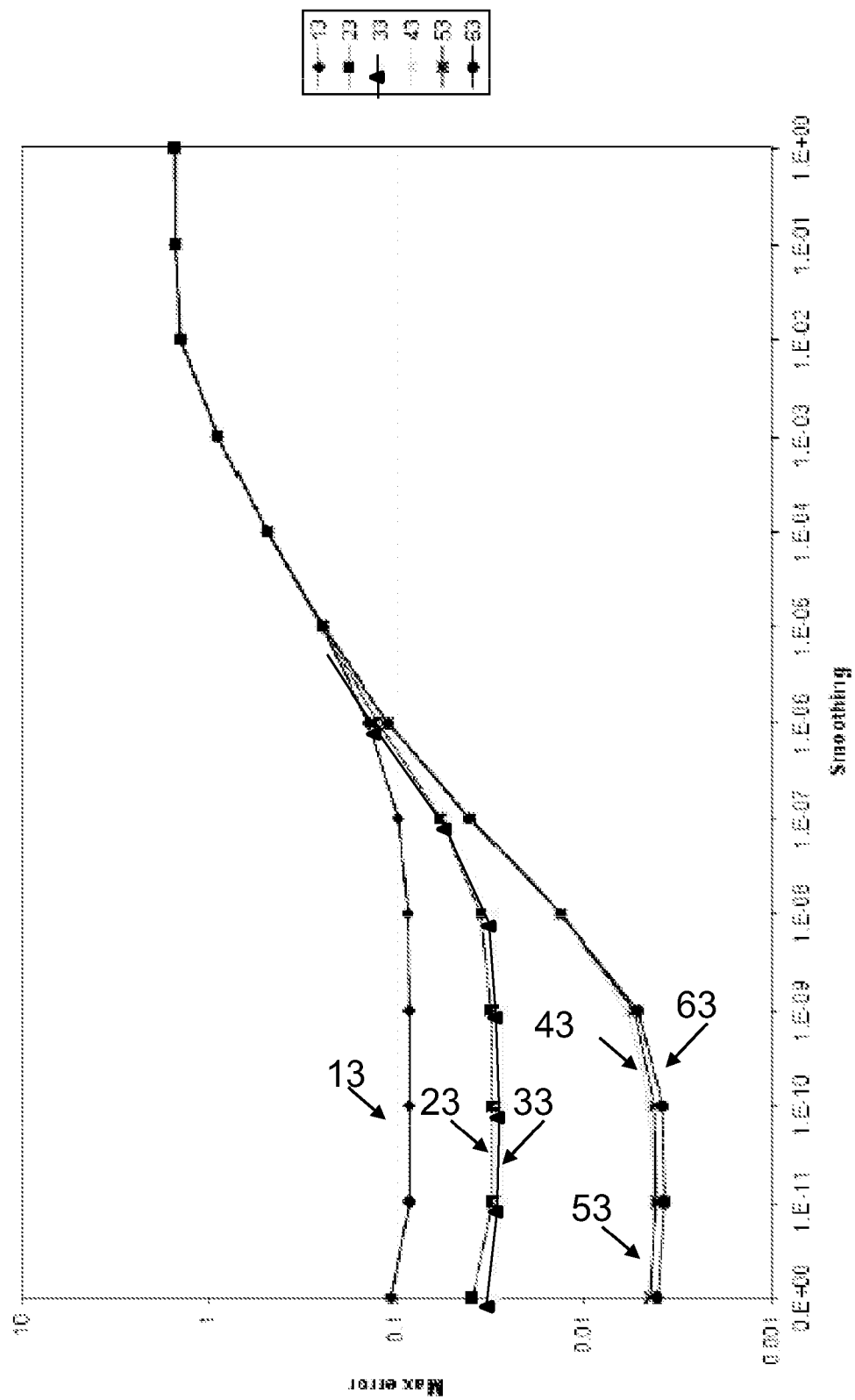
FIG. 15 illustrates a variation of the maximum fitting error with increasing smoothing parameter value in accordance with an aspect of the present invention.

FIG. 14 shows the variation of the least squares residual error with increasing smoothing parameter value. Each curve is labeled with a number that indicates the number of B-Spline control points (same in U and V). FIG. 15 shows the variation of the maximum fitting error with increasing smoothing parameter value. Each curve indicates variation for a given number of control points as labeled in the legend. The maximum fitting error is computed as the maximum of the distance of a sample to its closest point on the approximated surface. The two graphs are closely co-related. A more detailed analysis is provided below.

First, when smoothing is not used, the maximum error and the least squares residual error progressively decrease as the number of control points increases. This is expected since there are more degrees of freedom to approximate the shape of the data grid. However, as previously noted, such surfaces may have undesirable wiggles and the number of wiggles increases with control net size. Second, for any given control net size, the error growth with increasing smoothing parameter value can be distinguished into three regions. Initially, the error does not increase much. Then there is a point after which the error grows exponentially (linear in graph since it is shown on logarithmic scale). Finally, after a given value the accuracy of the surface is no longer preserved and the surfaces assume minimal curvature. At every iteration, the method estimates the value of the smoothing parameter a little to the right of end of the first segment by exponential interpolation. At this value, the surface will be smoother while at the same time will retain accuracy. Therefore, the goal of the iterative method is to determine the control net size as well as the desired smoothing parameter such that the maximum error bound is satisfied.

As an aspect of the present invention an iterative method is provided using least squares fitting with smoothing to automatically compute optimal number of control points, location of control points as well as smoothing parameter values. The surface fitting method is designed to reduce user assistance as much as possible. The user needs to specify two parameter values—one for the maximum allowed error and one for the amount of smoothness required. At each iteration, the knots are determined so that there is at least one sample within every knot interval. This is done so that the least squared system is positive definite. The method proceeds in the two phases:

Phase I: Determine minimum number of control points ($C_{min}$) such that surface is within maximum error bound using least squares approximation without smoothing. This is implemented using a binary search on the number of control points in the range degree+1 through $\min(m_r,m_c)$.

Phase II: Determine minimum number of control points such that surface is within maximum error bound and satisfies smoothness criterion using least squares approximation with smoothing. The smoothness condition for a given number of control points is deemed satisfied if the total error grows only by a user specified amount. This phase is implemented using a binary search on the number of control points in the range $C_{min}$ through $\min(m_r,m_c)$. For a given number of control points, the desired smoothing weight is iteratively estimated using exponential interpolation. The method stops when the maximum error bound is within the tolerance.

Figure 16:
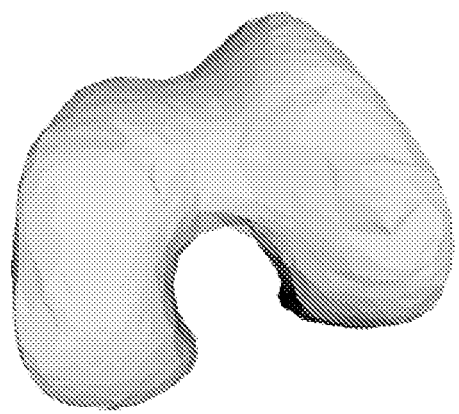
FIGS. 16 and 17 illustrate a knee implant region mesh extracted from a femur and a smooth and accurate surface fit using an aspect of the present invention.
Figure 17:
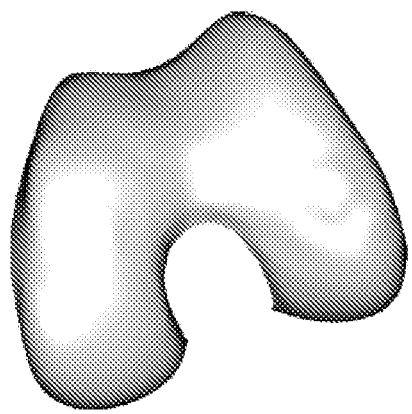

Typical values for the maximum allowed error are 0.01 or 0.001. From experiments it was determined that allowing a growth of the least squares residual by one or two orders of magnitude seems to give sufficiently smooth surfaces. FIG. 16 illustrates a knee implant region mesh extracted from a femur. FIG. 17 illustrates a smooth and accurate surface fit related to FIG. 16 using a method as provided herein as an aspect of the present invention. It has a 53 by 53 control net and with $\lambda=3.4\times10^{-7}$.

FIG. 17 shows the optimal surface computed using the above algorithm for a distal femur data set shown in FIG. 16. An alternative iterative algorithm that successively adds degrees of freedom instead of performing binary search is presented elsewhere herein.

For the data set shown in FIG. 16, the samples are relatively sparse near the front due to the distortion in parameterization. Surface quality may be additionally improved by performing weighted least squares.

Figure 18:
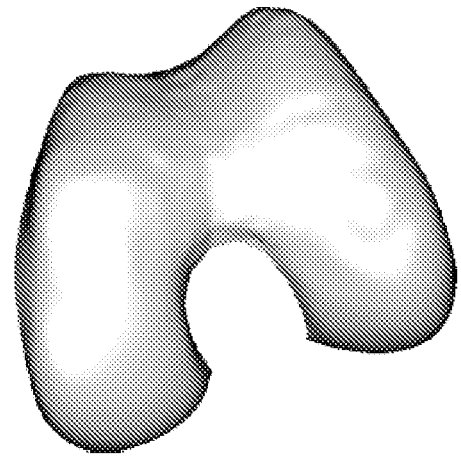
FIGS. 18 and 19 illustrate a comparison of surface fit without least square weights and with least squares weights in accordance with an aspect of the present invention.
Figure 19:
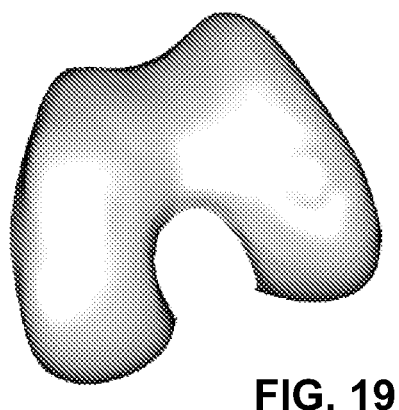

FIGS. 18 and 19 compare surfaces fit with and without weights, wherein FIG. 18 shows a surface without least square weights (64 by 64 control net, $\lambda=8.5\times10^{-9}$) and FIG. 19 shows a surface with least square weights (53 by 53 control net, $\lambda=3.4\times10^{-7}$). In this example, samples that are closer to the medial and lateral condyle ends were assigned weight value 10.0 since the parametric distortion in these regions results in sparser samples in the grid. FIG. 19 shows that one can get better quality surfaces by setting appropriate weights.

Figure 20:
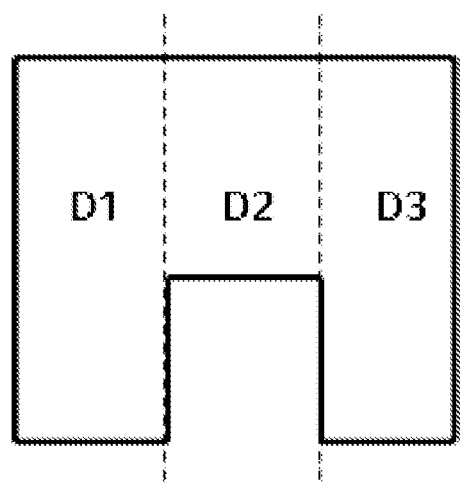
FIG. 20 illustrates a parametric domain template for distal femur in accordance with an aspect of the present invention.
Figure 27:
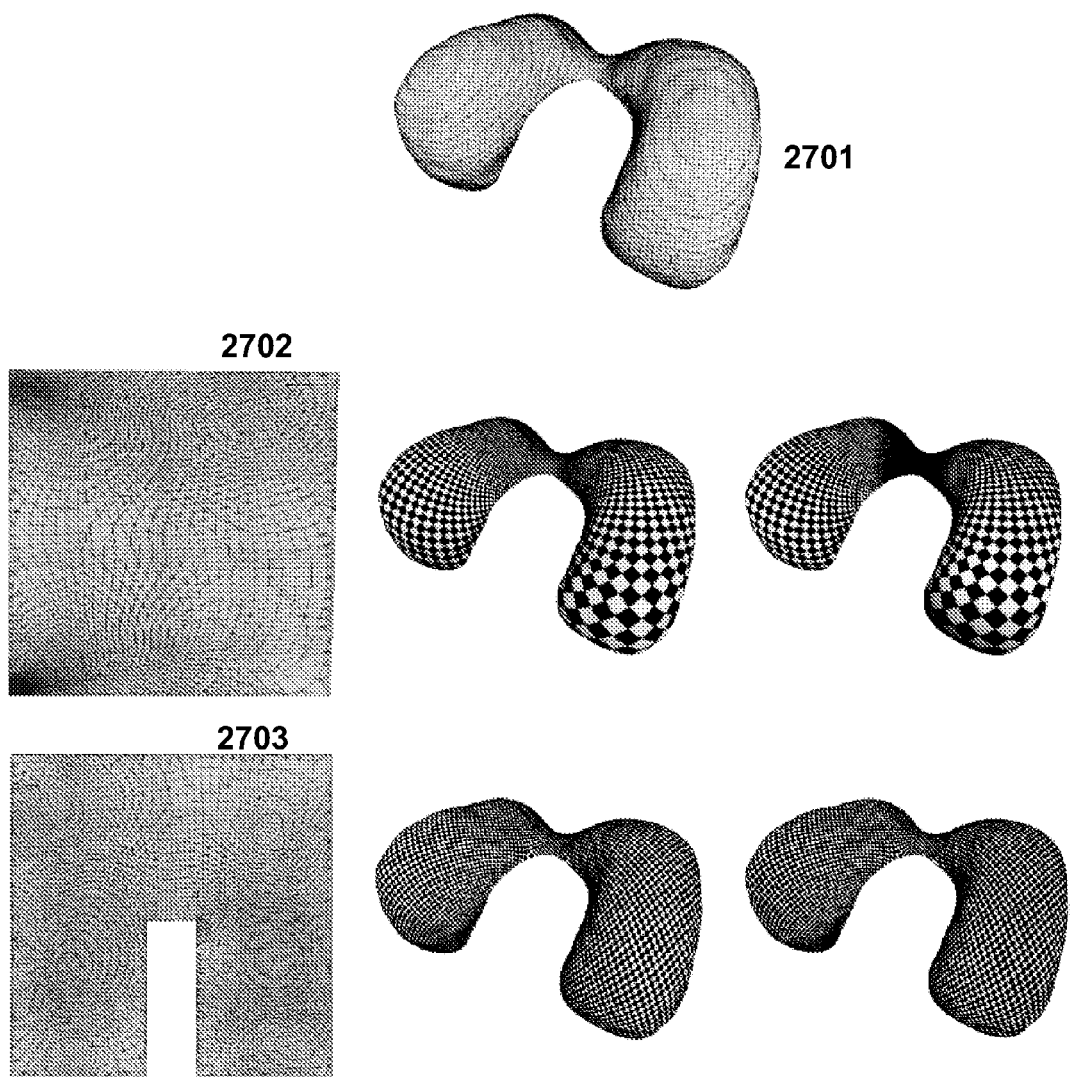
FIG. 27 illustrates the results of a knee bone model in accordance with an aspect of the present invention.

2) Multi-patch Fitting: The distal femur surface has a highly curved outer boundary with concave regions. For such surfaces, a rectangular parameter domain may result in large relative distortions as shown herein. This results in irregular sample grids that will not allow accurate B-Spline surface approximation in regions where sampling is sparse. In general, a polygonal template domain that more closely conforms to the shape of the outer boundary will result in less parametric distortion and therefore more regular sample grids. For the distal femur bone, a template illustrated in FIG. 20 has been chosen. This template domain gives better parameterization results than a rectangular domain as shown in FIG. 27. For surface fitting, the samples are divided into three patches with anatomical correspondences; D1 on left and D3 on right corresponding to condyles and D2 in center corresponding to the patellar surface. Surfaces are fit to the three patches so that $C^{(2)}$ continuity is obtained across shared patch boundaries. The chosen template also has particular advantages for distal femur surfaces since it enables creation of implants for partial knee replacements. This would involve fitting surfaces for only one of the condyles with or without the patellar surface.

The iterative method provided herein as an aspect of the present invention may be used to fit surfaces separately to patches D1 and D2. Also provided as an aspect of the present invention is another method that successively adds degrees of freedom where required. The left and right patches have simpler geometry as compared to the surface as a whole. As a side note, the successive approach when applied to the single patch surface took longer to complete since many more iterations were required.

Recall that in the iterative method provided herein, binary search is performed on the control net size in both phase I and II. The knot vectors at each step were determined based on the control net size and the distribution of samples. This algorithm starts from the minimum control net size (4×4 for a bicubic surface) and successively adds degrees of freedom (knots) in the regions of maximum error. If the same locations are requested multiple times, knots are added in neighboring regions to avoid placement of multiple knots that reduce B-Spline continuity. Knots are placed such that every knot interval has at least one sample.

Surfaces fitted separately to all three patches will not guarantee continuity and smoothness at shared patch boundaries. Therefore after fitting surfaces to patches D1 and D3 separately, a constrained surface is fitted to the central patch DD. $C^{(0)}$, $C^{(1)}$ and $C^{(2)}$ continuity conditions at the shared boundaries of D2 constrain the placement of the first three and last three control vertex columns of D2.

The number of control vertex rows and knots in the vertical direction for D2 are dictated by patches D1 and D3. The knots for the shared boundaries of D2 are refined to match D1 and D3. Additional knots and control vertices are added to satisfy a maximum error tolerance using an iterative algorithm that uses constrained least squares fitting in each step.

Figure 21:
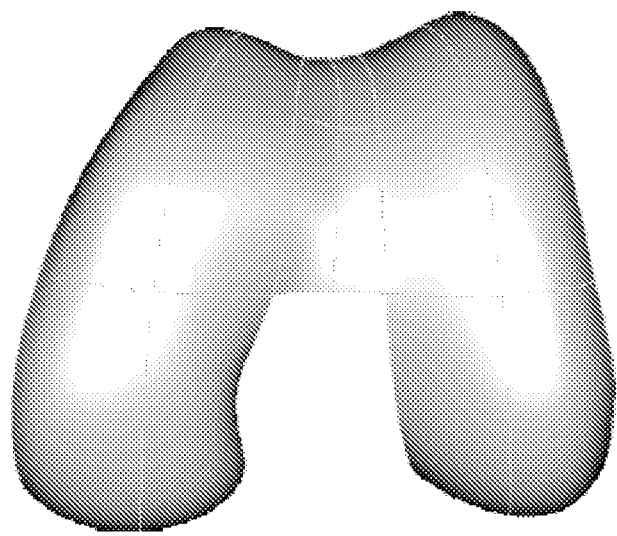
FIGS. 21 to 23 illustrate an optimal multi-patch surface fit to template based samples in accordance with an aspect of the present invention.
Figure 22:
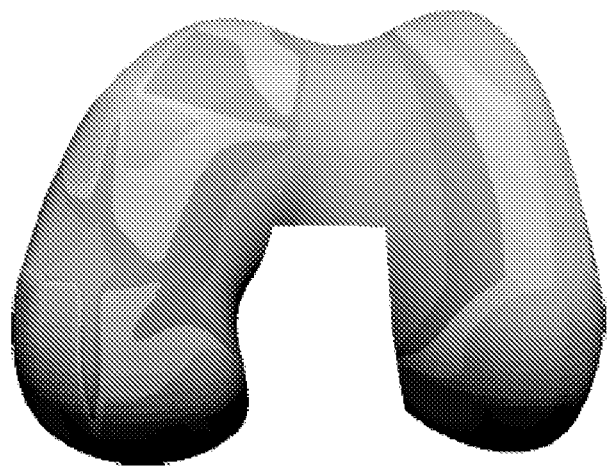
Figure 23:
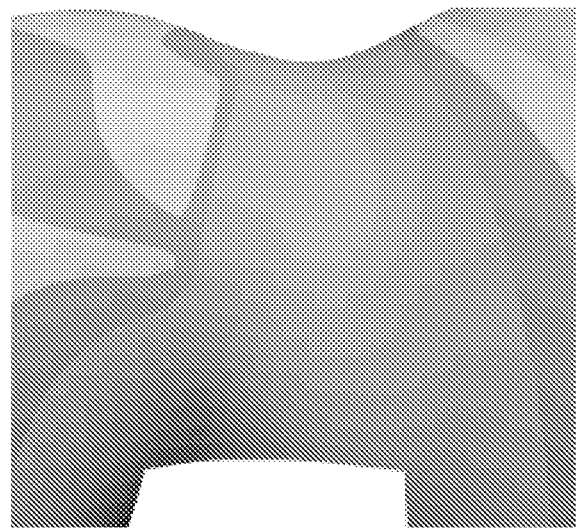

FIG. 21 shows an optimal multi-patch surface fit to template based samples. Patch D1 has 9×9 control points, patch D2 has 7×6 control points and patch D3 has 6×7 control points. The multi-patch surface has an order of magnitude fewer control points than the single patch surface that has $53^2$ control points. FIG. 22 shows a map of the Gaussian curvatures of the multi-patch surface. Smooth variation of the curvatures across shared boundaries confirms $C^{(2)}$ smoothness of the surface. FIG. 23 shows a magnified view of the map in the region around the central patch for further visual clarity.

F. CAD Model Creation

In order to convert a B-Spline surface to a thick solid model, an offset surface is first created along the surface normal direction. Isocurves corresponding to the boundaries of the original surface as well as the offset surface are extracted.

Ruled surfaces are created between corresponding pairs of boundary curves. The ruled surfaces are then stitched with the original and offset surfaces along respective common boundary curves. Features such as pins required to assemble the implant onto a patient's bone may be modeled separately and added to the implant solid model using Boolean operations. Other assembly features include screw threads.

Figure 24:
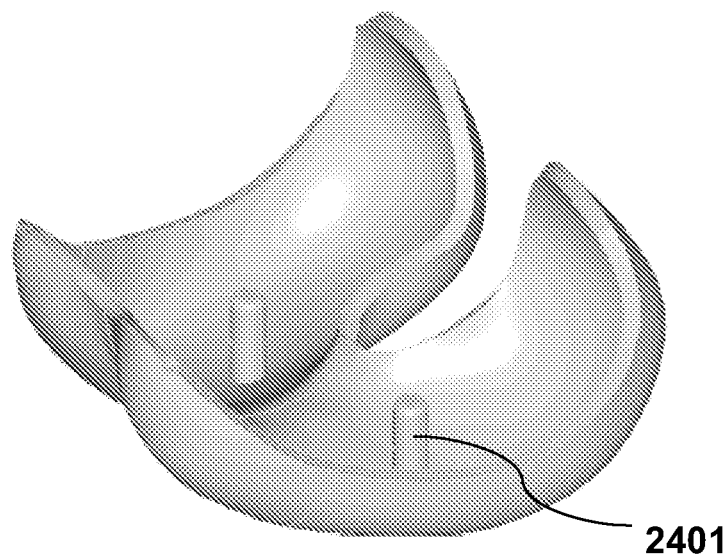
FIGS. 24 and 25 show solid models created from single and multipatch surfaces obtained from the iterative fitting process in accordance with an aspect of the present invention.
Figure 25:
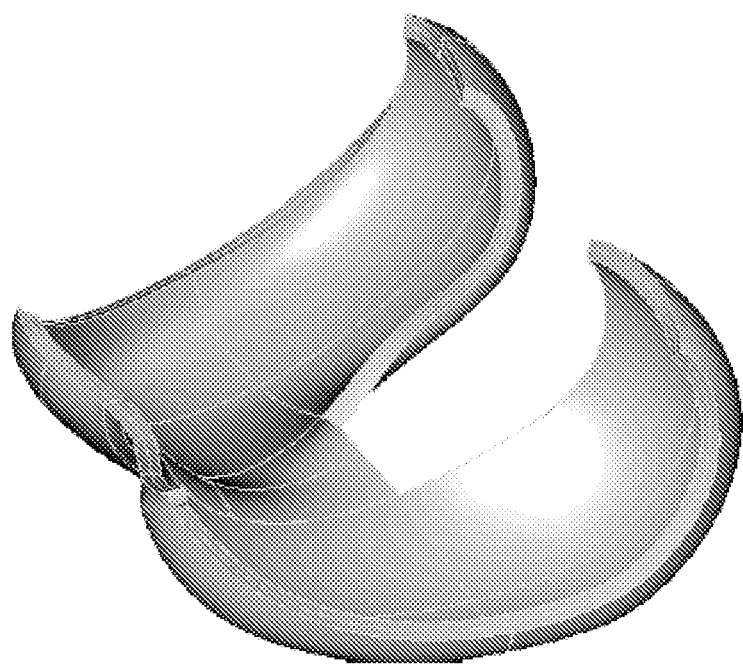

FIGS. 24 and 25 illustrate solid models of implants created from B-spline surfaces, with FIG. 24 being a single patch surface with pins of which a pin 2401 is identified and FIG. 25 a multi-patch surface.

FIG. 24 shows solid models created from single and multipatch surfaces obtained from the iterative fitting algorithm. The solid models are then exported to standard CAD formats such as IGES or STEP that can then be sent to a CAM system for manufacturing. Solid model creation, assembly feature addition and CAD format export was performed using OpenCascade as described in S. Open Cascade, "Open cascade technology ver 6.3," 2010, URL-www.opencascade.org.

Results from Other Data Sets

Next some results of the parameterization are shown. The methods described were tested on an Intel Pentium D 2.8 GHz PC with 2 GB RAM. They were implemented in C++ and compiled by Microsoft Visual Studio 2008. Matlab R2008a was used as the linear system solver. In all tests where the maximum number of vertices of the models is approximately 20,000, the running time is less than 2 seconds. Later in this section the pros and cons of the different parameterization methods for the application of reverse engineering will also be analyzed.

Figure 26:
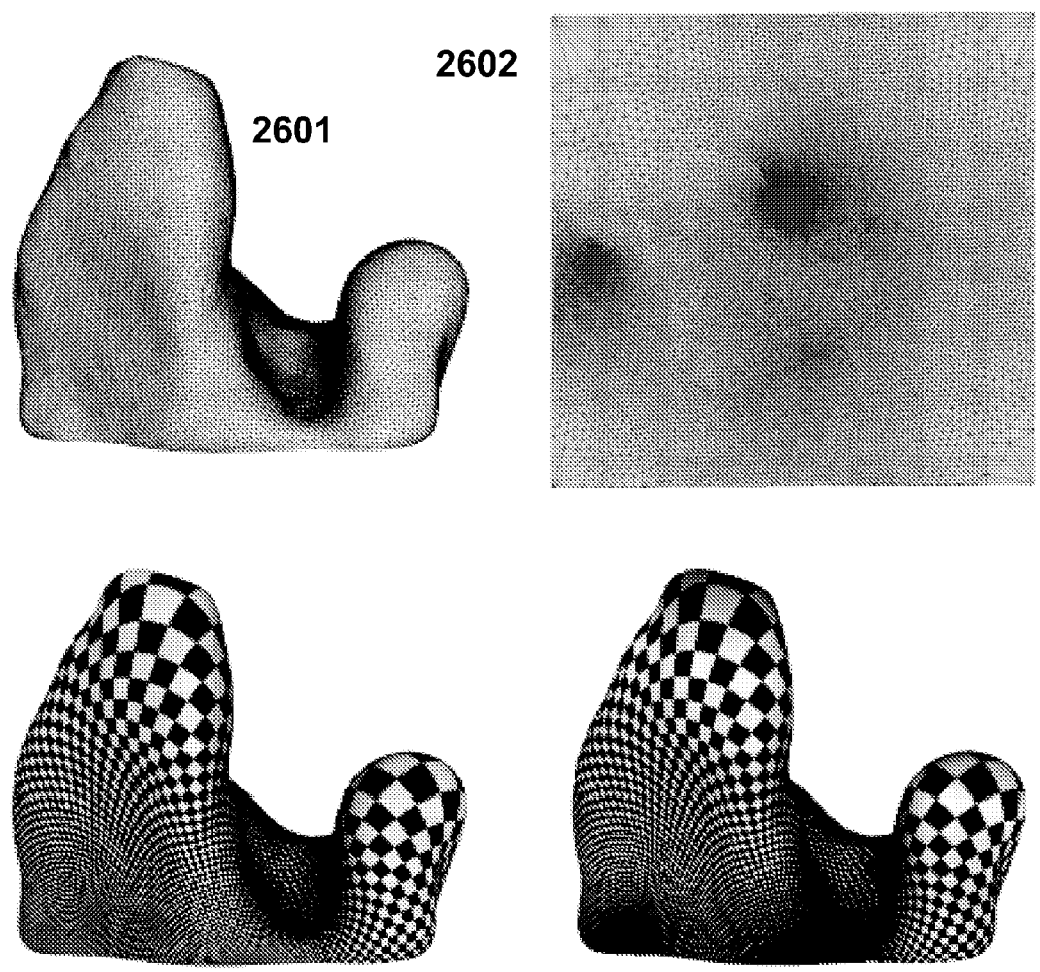
FIG. 26 illustrates a parameterization result of a hearing aid model in accordance with an aspect of the present invention.

In FIG. 26 the parameterization result of a hearing aid 2601 to a unit square 2602 is shown. On top right in 2602 a (u, v) coordinate for each vertex of the original mesh is assigned, and thus flatten the model to a planar square. On bottom left that coordinate is used as the texture coordinate, a check-board as the texture, and employ texture mapping. From the figure, one can see that the intersection angle of iso-parametric lines is nearly 90 degree, which demonstrates the low stretch, or angle distortion of the mapping. However, as stated earlier, if the mapping is angle-preserving, then usually there should be area distortion, or metric distortion. On the bottom right of FIG. 26 a further mapping illustrates this.

Figure 28:
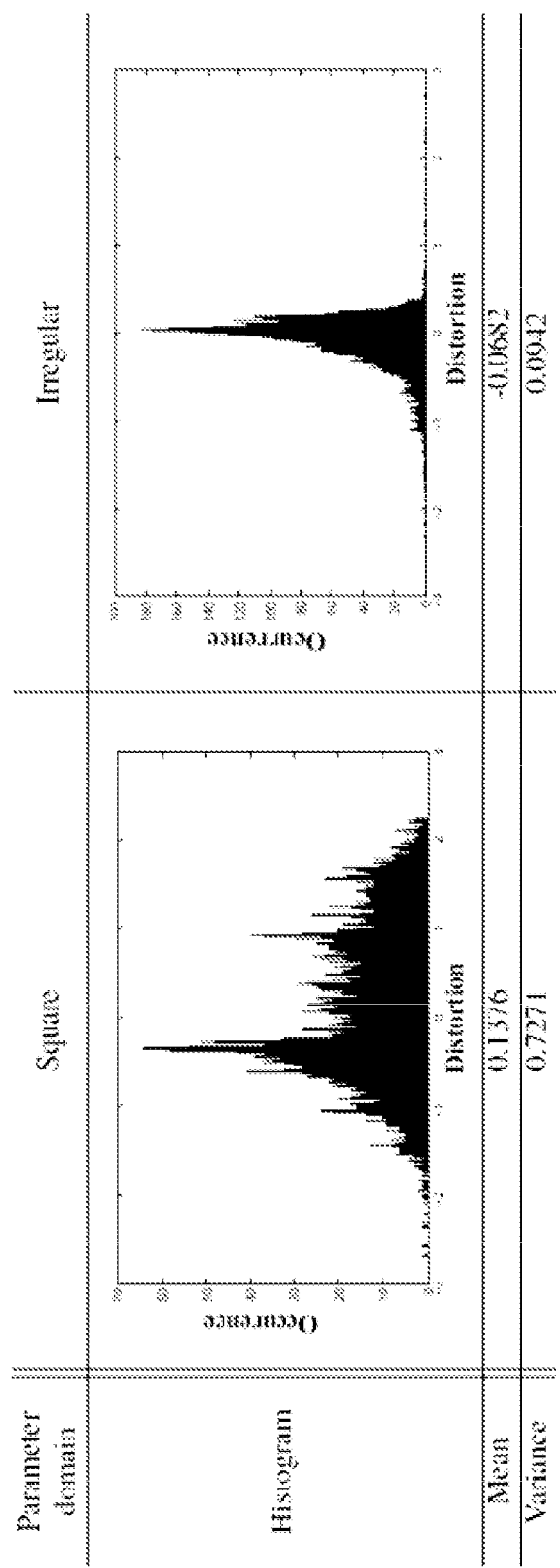
FIG. 28 illustrates the low distortion of the multipatch parameterization in accordance with an aspect of the present invention.
Figure 29:
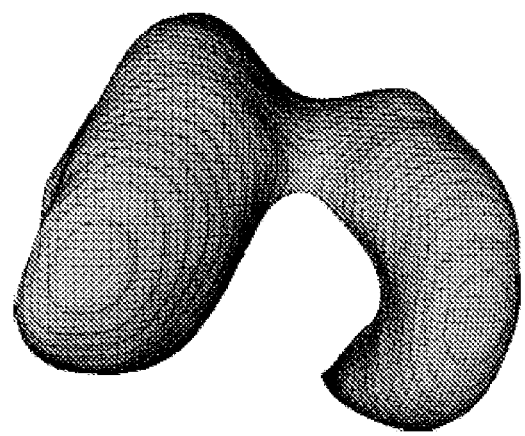
FIGS. 29 to 31 illustrate the processing of a distal femur bone in accordance with an aspect of the present invention.
Figure 30:
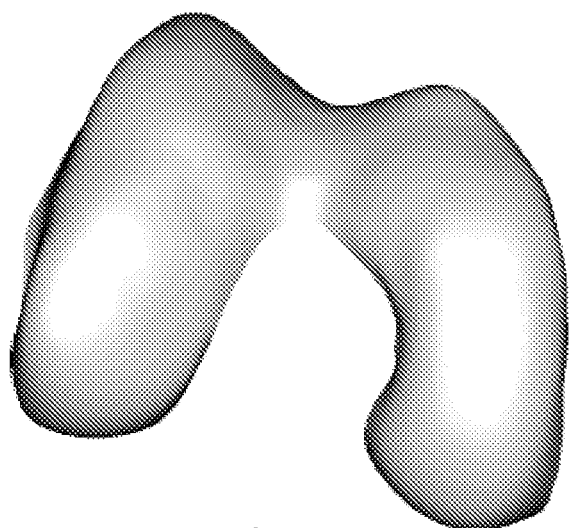
Figure 31:
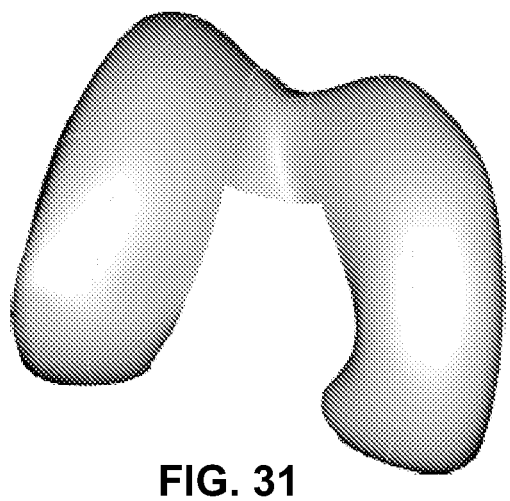

The above method has also been tested on a knee bone model in a similar manner as described above. Due to the apparent concavity of its boundary, it was also tried to map it to an irregular planar. FIG. 27 illustrates the results of a knee bone model. The first row in 2701 shows the original triangulation. The second and third rows show the planar domain, the texture mapping, and the map of the area distortion of two different parameter domains respectively, similar to what has been done in FIG. 26. FIG. 28 demonstrates the low distortion of the multipatch parameterization. FIG. 29 shows a polygonal mesh of a distal femur bone obtained after processing a CT scan image. FIG. 30 shows a single surface patch fit to the mesh after parameterization and grid sampling using the techniques presented herein in accordance with an aspect of the present invention. FIG. 31 shows a template based multi-patch surface fit to the mesh. The outer boundary of the multi-patch surface seems to have sharper corners. This is due to the fact that the mesh parameterization generated degeneracies at the corners due to the poor quality of the mesh triangulation in these regions. Therefore a small area of the mesh near the boundary was chopped and not used for surface fitting. Such degeneracies may be avoided by remeshing the data to obtain better quality triangulations and reparameterizing the new meshes.

In summary, as an aspect of the present invention a complete workflow for creating CAD models of patient-specific customized implants from scanned medical images has been provided. One implementation demonstrates the medical images. One implementation demonstrates the feasibility of creating a unified system to perform all tasks in the proposed pipeline viz., image processing, discrete surface creation and processing, smooth surface creation and solid model creation and processing. A unified system as provided herein enables faster turnaround times for creating customized implants of better quality, thereby improving the market potential of a product based on it.

Anatomical objects typically have highly curved complicated surface geometry. In particular, techniques for mesh parameterization, sampling, single and multi-patch surface fitting, and solid model creation were implemented. The techniques have been demonstrated for the application of creating distal femur implants for knee replacements. The distal femur surface is highly curved, has a highly curved outer surface boundary with concave regions resulting in two finger like extensions (condyles) and a central connecting region (patellar surface). The results indicate that the techniques provided herein as one or more aspects of the present invention are well suited for the problem.

The template based parameterization and successive multipatch surface fitting in particular seems to have potential for fitting other anatomical objects with complicated geometry.

In one embodiment of the present invention, appropriate template shapes are selected for each type of anatomical object and the parameterization and surface fitting techniques are extended for the chosen templates.

Figure 32:
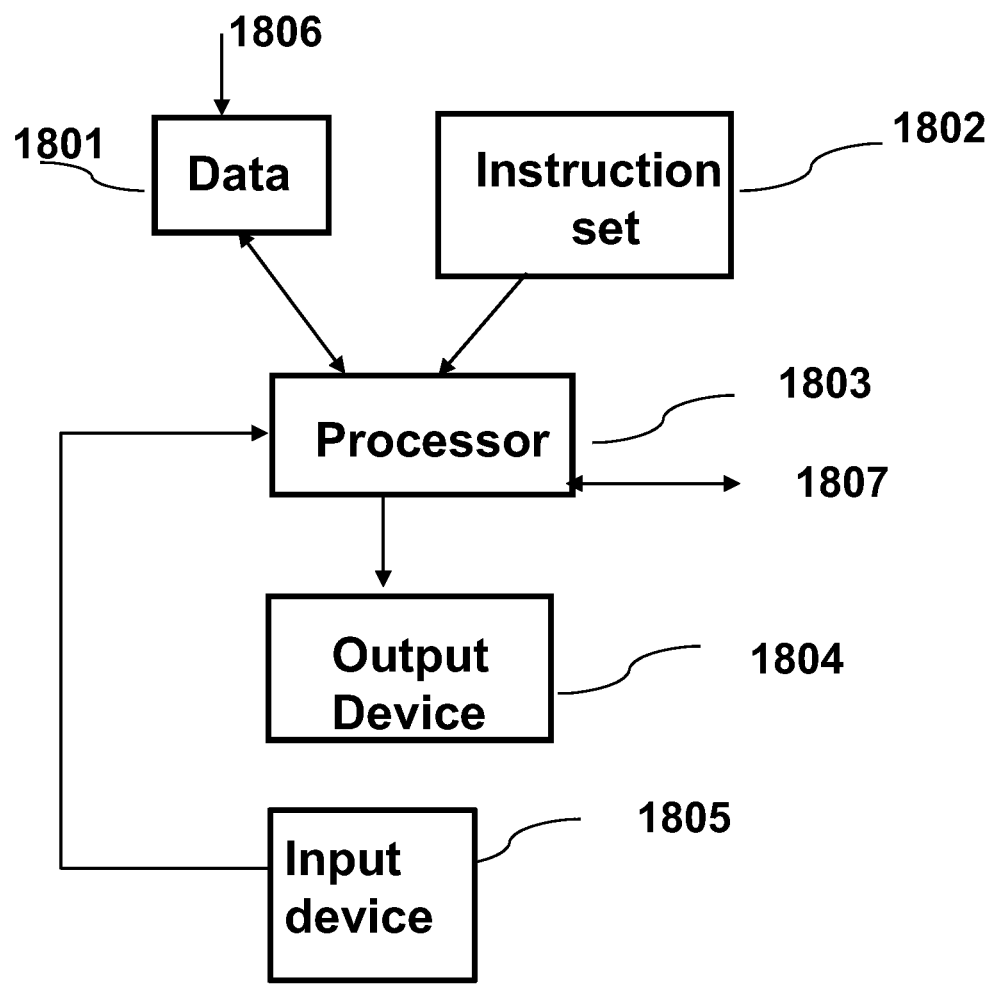
FIGS. 32 to 33 illustrate a system used to perform the processing steps set forth above in accordance with various aspects of the present invention.

A system illustrated in FIG. 32 and as provided herein as an aspect of the present invention is enabled to receiving, processing and generating data. The system is provided with data that can be stored on a memory 1801. Data may be obtained from a data source, for instance via an input 1806. Such data may be medical image data or any other image data. The data may also be CAD data such as a CAD model of a medical implant. The system has a processor 1803. The processor 1803 is provided or programmed with an instruction set or program executing the methods of the present invention that is stored on a memory 1802 and is provided to the processor 1803, which executes the instructions of 1802 to process the data from 1801. Data, such as image data or CAD data or CAM data such as a CNC file or any other signal resulting from the processor can be outputted on an output device 1804, which may be a display to display data or a data storage device. The output device may also be a storage device that stores the outputted data. Device 1804 may also be a communication device to a manufacturing machine such as a CNC machine or any other CAM machine.

Device 1804 may also be a display that displays the generated CAM data in relation to a medical image. The processor also has a communication channel 1807 to receive external data from a communication device and to transmit data to an external device. The system in one embodiment of the present invention has one or more input devices 1805, which may be a keyboard, a mouse or any other device that can generated data to be provided to processor 1803. The processor can be dedicated hardware. However, the processor can also be a CPU or any other computing device that can execute the instructions of 1802. Accordingly, the system as illustrated in FIG. 32 provides a system for data processing resulting from a sensor such as medical image data or any other data source and is enabled to execute the steps of the methods as provided herein as an aspect of the present invention.

Figure 33:
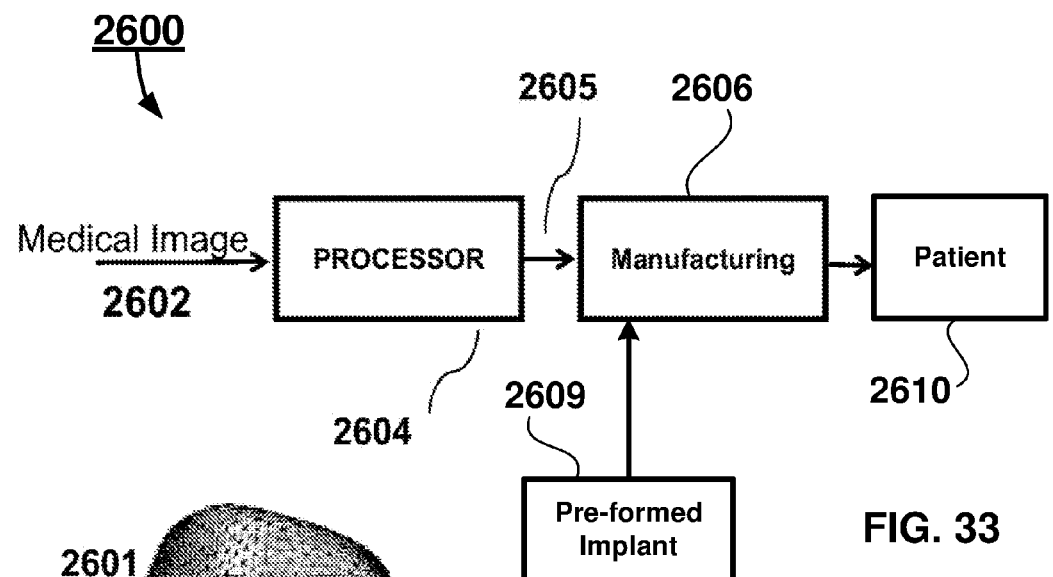

The methods as provided herein are, in one embodiment of the present invention, implemented on a system or a computer device. FIG. 33 illustrates a system 2600 used in generating CAM model of an implant in accordance with an aspect of the present invention. A processor 2604 is programmed to perform the steps of a method provided herein in accordance with an aspect of the present invention. On an input 2602 data related to a medical image of a patient, such as a patient bone such as a distal femur, is received. The processor processes the image data as described above to provide CAM model of a medical implant with a match between the generated medical implant and the patient's bone and outputs a data file representing the CAM model of the medical implant on 2605. Output 2605 may be connected to a manufacturing system 2606 that is enabled to provide the actual medical implant in its appropriate shape. For instance the CAM model may be provided or transformed into CNC instructions to a CNC machine that mills a material into the medical implant. In a next step the medical implant generated from the CAM model is removed from the manufacturing machine 2606 and implanted in a patient 2610 for instance by a surgeon.

There may be a choice of material for the implant that can be selected or the selected implant will be manufactured in one pre-determined material. In any event, in one embodiment of the present invention data of an implant related to patient image data is provided with manufacturing data related to manufacturing system 2606. For instance, if 2606 includes a CNC machine, then data related to cutting tools, preferred milling speeds and other data related to machining a piece of a pre-determined material is attached to the CAM file, so that the set-up of the manufacturing machine can be done based on data that is part of the customized CAM file. In a further embodiment of the present invention, an order of milling steps by manufacturing machine 2606 may be done based on an analysis of the customized CAM file. In a further embodiment an order of at least two milling or cutting steps may be pre-set in the CAM file, including a switching of tools. Availability of such data will minimize the need for pre-manufacturing planning and human intervention during manufacturing.

In one embodiment of the present invention an image storage device or a medical imaging device, the system 2604 and the manufacturing system 2606 are all connected via a network. In a further embodiment the network is the Internet. In yet a further embodiment of the present invention the system 2604 is authorized to receive data 2602 and 2606 is authorized to receive data 2605 from 2604 over the Internet.

In one embodiment of the present invention, the implant is already manufactured in oversized format, and wherein customization includes the removal of excess material to achieve the final and customized dimensions of the custom implant. This allows a core of an implant, which in many cases is the same for different patients, to be pre-manufactured. This allows for a fine-tuning of a custom implant that in many cases is faster than building an implant from scratch. The manufacturing machine to that purpose is provided with high accuracy measuring equipment that determines the actual dimensions of a pre-formed implant 2609 as shown in FIG. 33. Based on the received CAD or CAM file the pre-formed implant 2609 is milled to the exact measurements required for the custom implant.

In one embodiment of the present invention a manufacturing machine is a deposit machine which deposits material based on instructions which are derived from the CAD or CAM file. In that case a pre-form is a skeleton structure that is under-sized compared to the final dimensions of the custom implant. The manufacturing machine is equipped with high accuracy measuring devices. Material is deposited onto the skeleton or preform and measured until the desired dimensions have been achieved.

The finalized custom implant is removed from the manufacturing machine. It may undergo additional treatment, including finalizing treatment such as annealing, hardening, polishing, sterilizing testing, marking or any other treatment that is required to prepare for surgical insertion. The custom implant is provided to a surgeon or a surgical robot in an operating room and is implanted in the patient.

Thus, methods and systems are provided to create a customized medical implant or a patient specific medical implant based on a medical image of the patient and to create a CAD model of an implant that corresponds to an image of a bone or an organ of the patient, and to provide the CAD file to a manufacturing machine to manufacture the patient specific medical implant.

Figure 34:
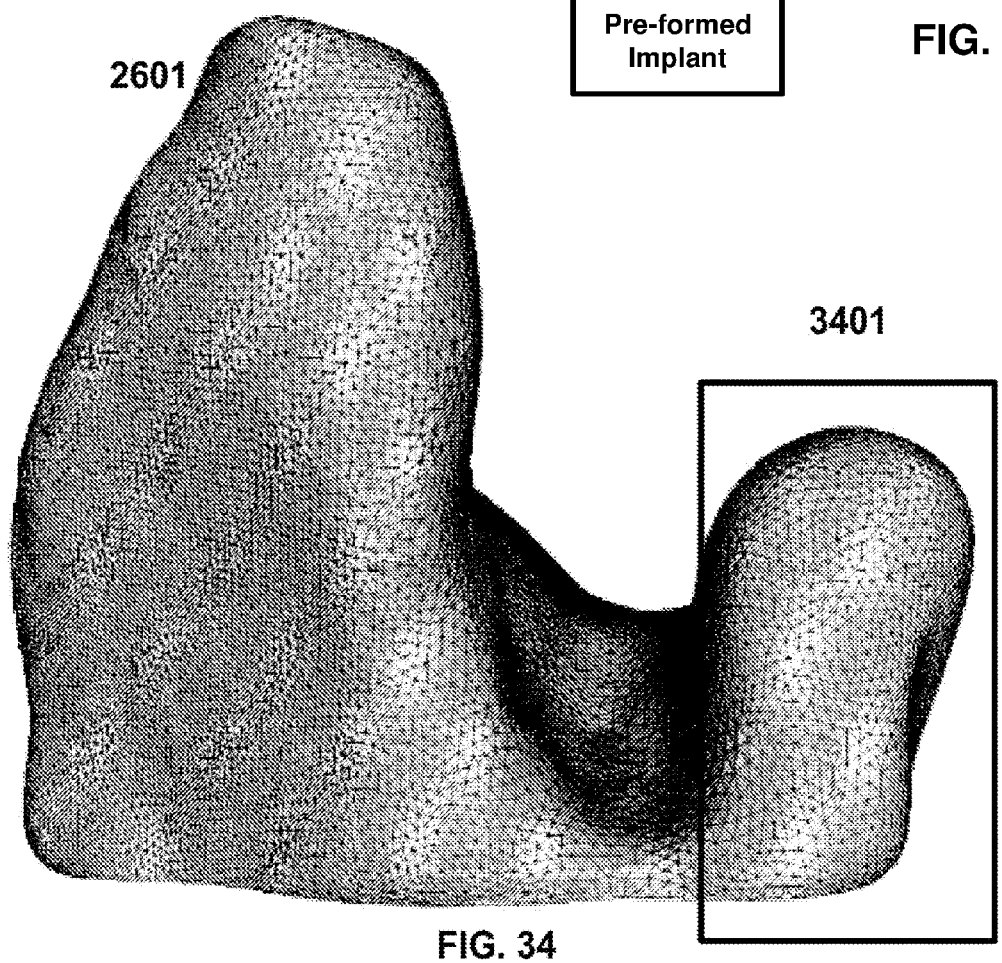
FIGS. 34 to 43 show detailed parts of FIGS. 26 and 27.
Figure 35:
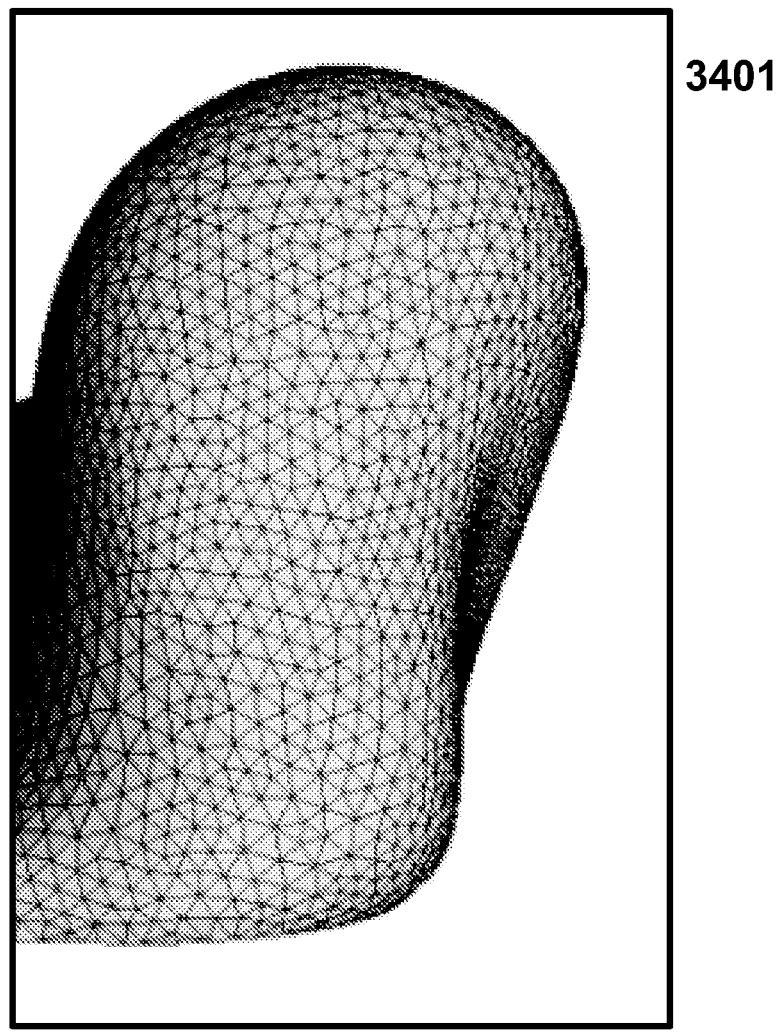
Figure 36:
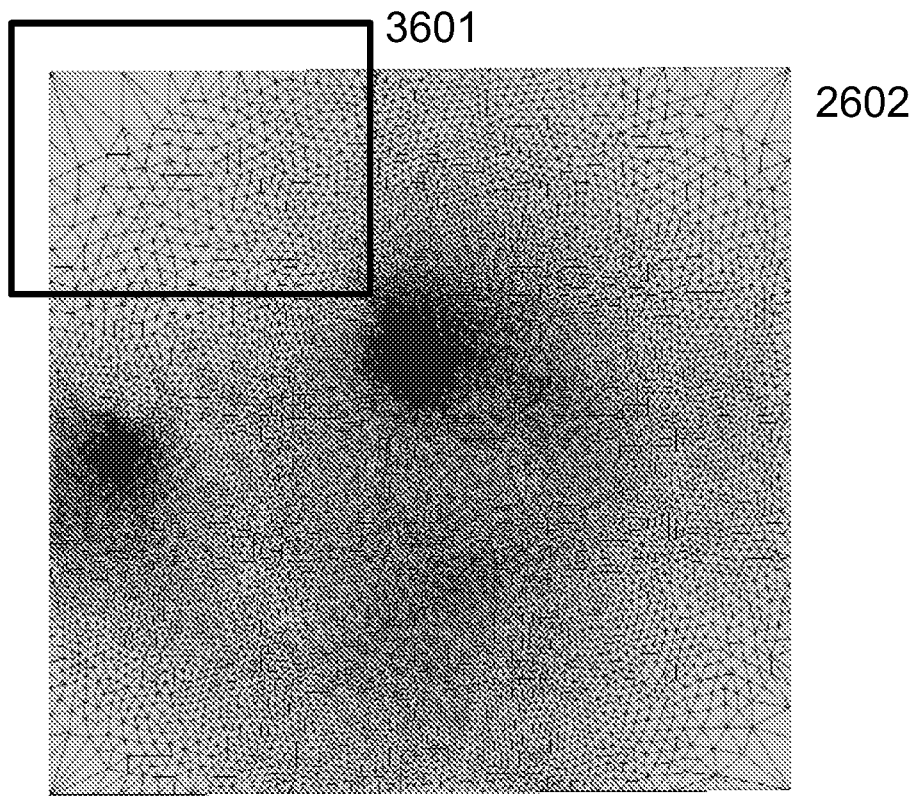
Figure 37:
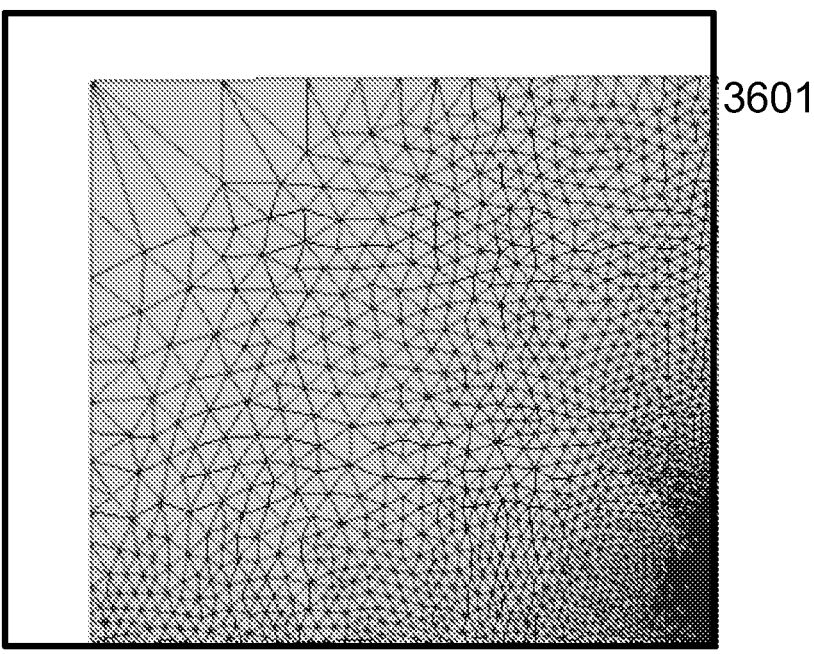
Figure 38:
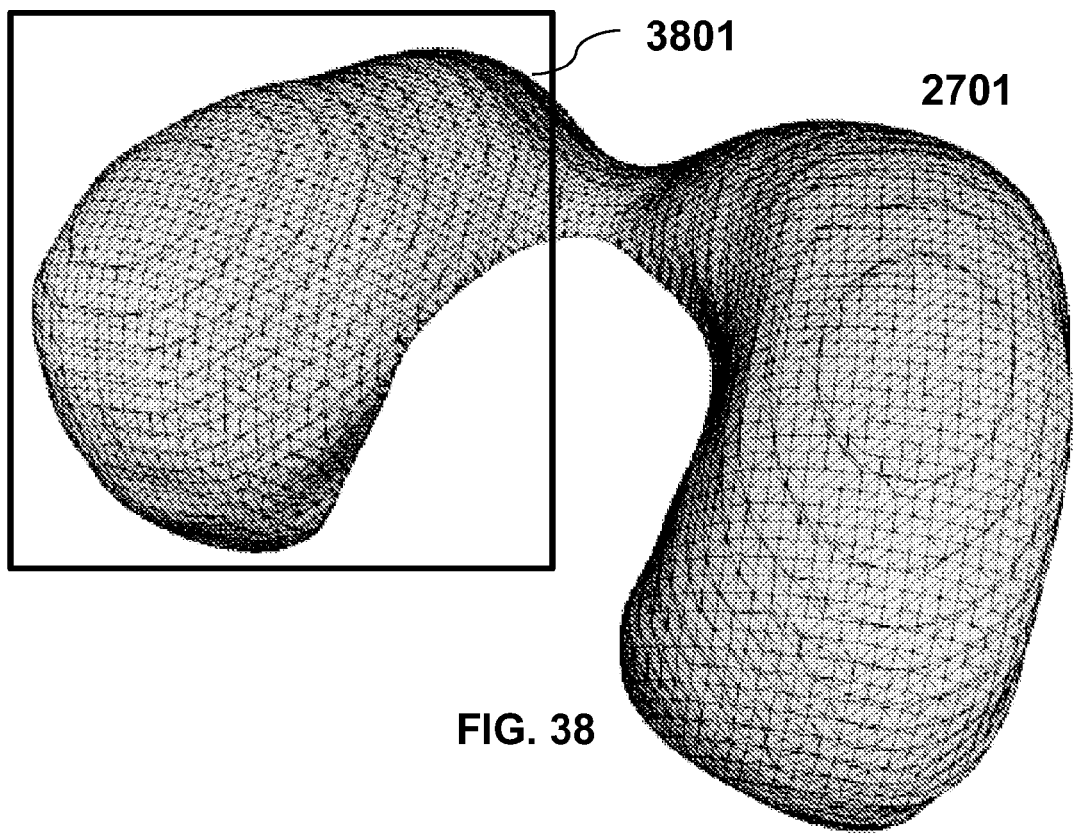
Figure 39:
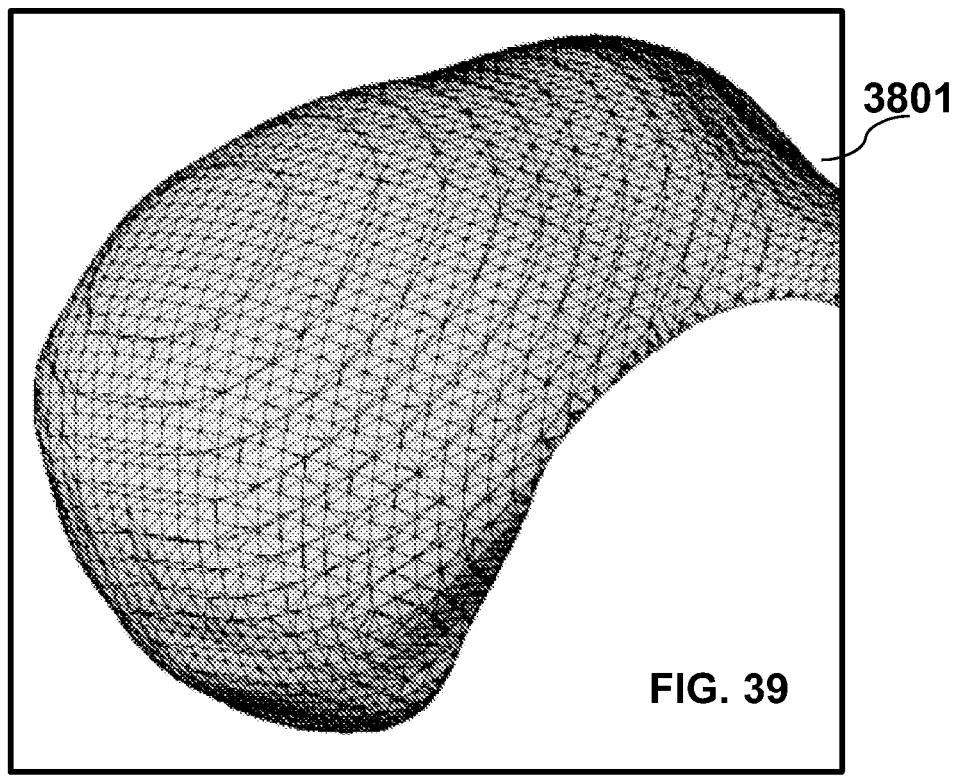
Figure 40:
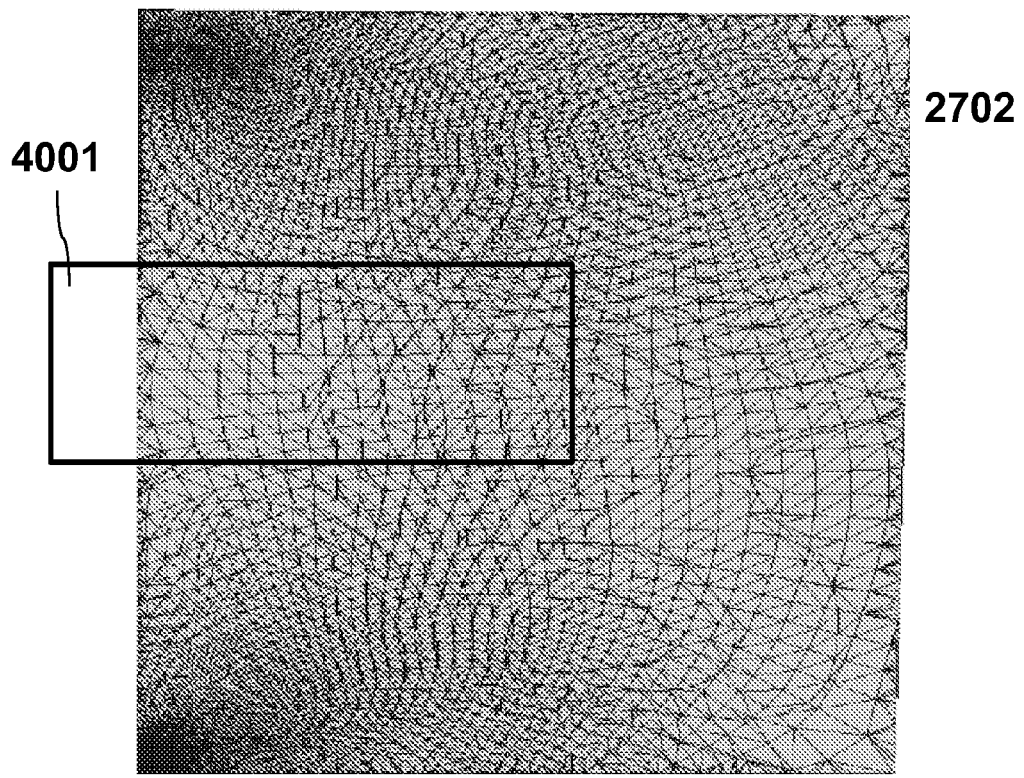
Figure 41:
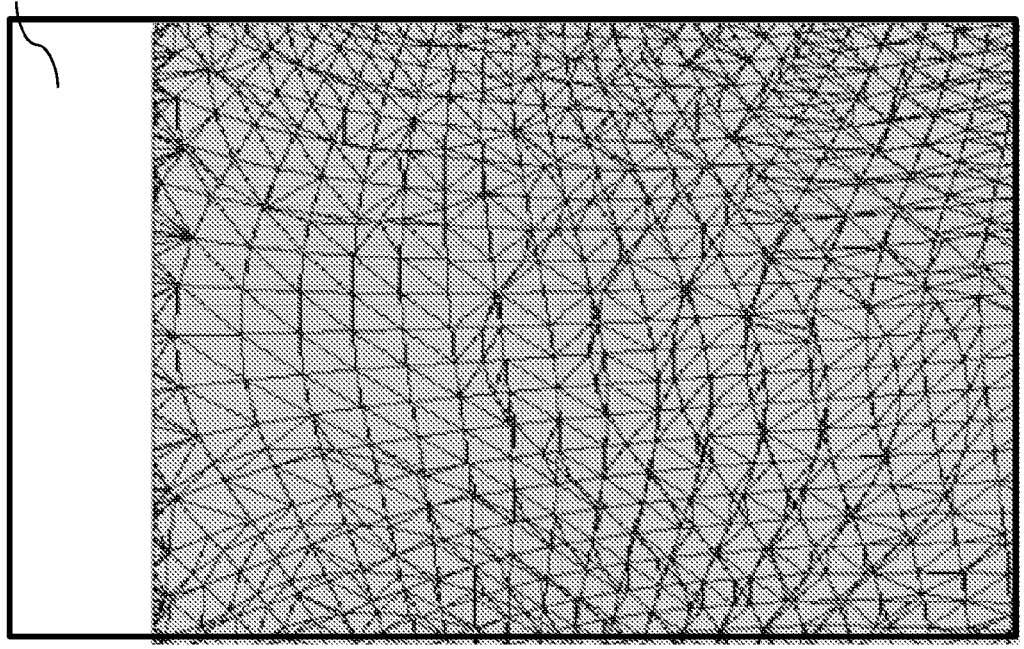
Figure 42:
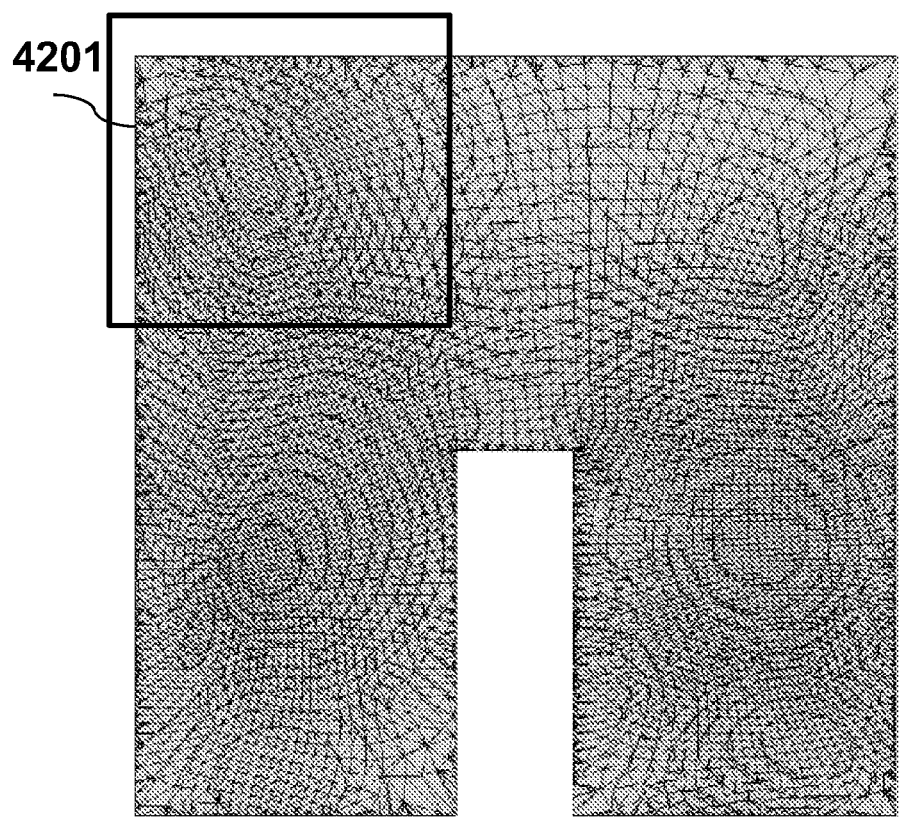
Figure 43:
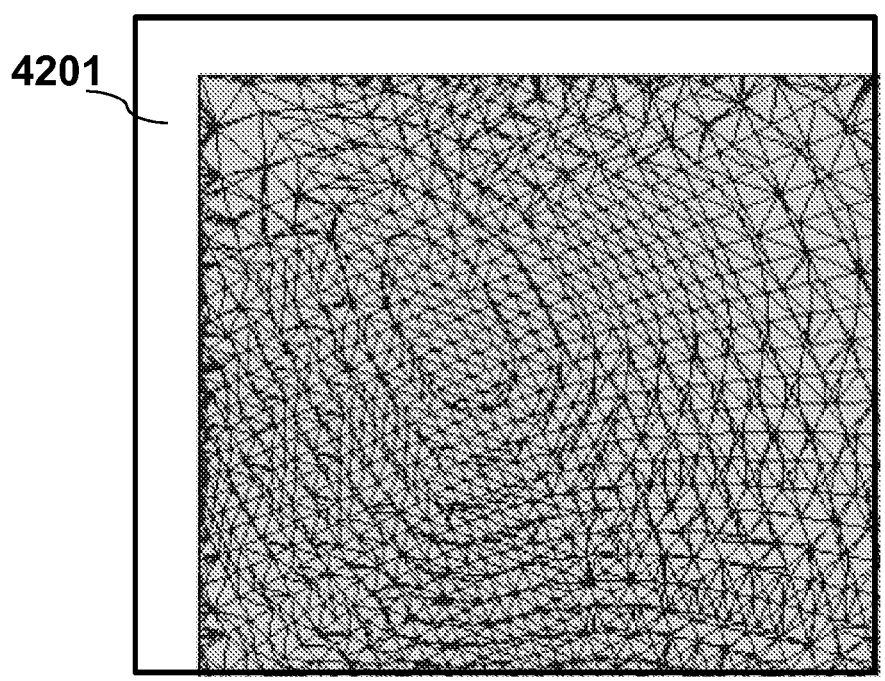

In order to further illustrate some of the steps of the present invention, triangulated figures have been enlarged to show a more detailed figure. Items 2601 and 2602 are shown enlarged in FIGS. 34-37. FIG. 34 illustrates an enlarged item 2601 which now shows the triangulation with a part 3401 which is shown in further enlargement in FIG. 35. FIG. 36 shows an enlarged 2602 and FIG. 37 shows an enlarged part 3601 in 2602. FIG. 38 shows element 2701 of which an enlarged part is shown in FIG. 39. FIG. 40 shows enlarged 2702 from FIG. 27 and part 4001 is further enlarged in FIG. 41. FIG. 42 shows part 7703 from FIG. 27 and part 4201 is further enlarged in FIG. 43.

In summary, in accordance with one aspect of the present invention, a method of making an implant from an image of a bone is provided. A processor receives image data of the image of the bone, segments a desired bone from the image data to create a segmentation of the desired bone, creates a polygonal mesh from the segmentation of the desired bone, extracts a part of the polygonal mesh corresponding to an implant region and parameterizes the part of the polygonal mesh so that every vertex therein is associated with two parameter values. The processor also resamples the polygonal mesh to generate a grid of 3D points regularly spaced in parametric domain and fits a B-spline surface to the grid using a least squares process, which can be weights. The processor can also smooth the surface.

Also in summary, in accordance with another aspect of the present invention, a method of making a patient specific implant is provided. In accordance with this method, an image of a portion of a patient's bone is taken. A processor is used to select a portion of the image to form a selected part of the image and processes the selected part of the image to form a surface. The processor creates a CAD model from the surface. Then a CAM system is used to manufacture the patient specific implant based on the CAD model. The method also comprising implanting the patient specific implant in the patient. In accordance with another aspect of the present invention, the CAM system can manufacture the customized medical implant from a preformed implant.

A solid CAD model can be created from the B-spline surface. Assembly features can be added to the CAD model. The assembly features can be a pin and screw thread. The implant can be manufactured using a CAM system. The polygonal mesh can be created using a Marching Cubes process or an Afront process or any other applicable process.

The following references provide background information generally related to the present invention and are hereby incorporated by reference: [1] W. Lorensen and H. Cline. "Marching cubes: A high resolution 3d surface construction algorithm," in *Proceedings of the 14th annual conference on Computer graphics and interactive techniques*. ACM. 1987. p. 169; [2] J. Schreiner. C. Scheidegger. and C. Silva. "High-quality extraction of isosurfaces from regular and irregular grids," *IEEE Transactions on Visualization and Computer Graphics*, pp. 1205-1212, 2006; [3] M. S. Floater and K. Hormann, "Surface parameterization: a tutorial and survey," in *In Advances in Multiresolution for Geometric Modelling*. Springer, 2005, pp. 157-186; [4] A. Sheffer, E.

Praun, and K. Rose, "Mesh parameterization methods and their applications," in *Foundations and Trends in Computer Graphics and Vision.* Now Publishers, 2006, pp. 105-171; [5] M. O. Carmo, *Differential Geometry of Curves and Surfaces.* Prentice Hall, 1976; [6] E. Cohen, R. Riesenfeld, and G. Elber, *Geometric modeling with splines: an introduction.* AK Peters Ltd, 2001; [7] L. Piegl and W. Tiller, *The NURBS book.* Springer Verlag, 1997; [8] C. De Boor, *A practical guide to splines.* Springer Verlag, 2001; [9] M. Botsch, M. Pauly, L. Kobbelt, P. Alliez, B. Levy, S. Bischoff, and C. Rossi, "Geometric modeling based on polygonal meshes," in *SIGGRAPH '07: ACM SIGGRAPH 2007 courses.* New York, N.Y., USA: ACM, 2007; [10] U. Pinkall and K. Polthier, "Computing discrete minimal surfaces and their conjugates," *Experimental Mathematics*, vol. 2, pp. 15-36, 1993; [11] V. Weiss, L. Andor, G. Renner, and T. Varady, "Advanced surface fitting techniques," *Computer Aided Geometric Design*, vol. 19, no. I, pp. 19-42, 2002; and [12] S. Open Cascade, "Open cascade technology ver 6.3," 2010, URLwww.opencascade.org.

While there have been shown, described and pointed out fundamental novel features of the invention as applied to preferred embodiments thereof, it will be understood that various omissions and substitutions and changes in the form and details of the methods and systems illustrated and in its operation may be made by those skilled in the art without departing from the spirit of the invention. It is the intention, therefore, to be limited only as indicated by the scope of the claims.

The invention claimed is:

1. A method of making an implant from an image of a bone, comprising:
   a processor receiving image data of the image of the bone;
   the processor segmenting a desired bone from the image data to create a segmentation of the desired bone;
   the processor creating a polygonal mesh from the segmentation of the desired bone;
   the processor extracting a part of the polygonal mesh corresponding to an implant region;
   the processor parameterizing the part of the polygonal mesh so that every vertex therein is associated with two parameter values;
   the processor resampling the polygonal mesh to generate a grid of 3D points spaced in a predetermined distance in parametric domain;
   the processor fitting a B-spline surface to the grid using a least squares process, wherein involves minimizing $$F_{smooth}(Q) = \sum_{k=0}^{r} w_k^2 \|S(u_k, v_k) - P_k\|^2 +$$
$$\lambda \sum_{k=0}^{r} (\|S_{uu}(u_k, v_k)\|^2 + \|S_{uv}(u_k, v_k)\|^2 + \|S_{vv}(u_k, v_k)\|^2)$$

where $w_k$ is a weighting coefficient, $S(u_k, v_k)$ is a surface, $P_k$ are sample points, $\lambda$, is a smoothing parameter, and $S_{uu}$, $S_{uv}$ and $S_{vu}$ are the second derivatives of the surface $S(u_k, v_k)$;
   the processor sending a computer-aided manufacturing (CAM) file based on the B-Spline surface fitted to a manufacturing machine; and
   the manufacturing machine forming the implant based on instructions derived from the CAM file.

2. The method of claim 1, comprising creating a solid computer-aided design (CAD) model from the B-spline surface.

3. The method of claim 2, comprising adding assembly features to the CAD model.

4. The method of claim 3, wherein the assembly features comprise one or more assembly pins.

5. The method of claim 3, comprising manufacturing the implant using a CAM system.

6. The method of claim 1, wherein the polygonal mesh is created using a Marching Cubes process.

7. The method of claim 1, wherein the polygonal mesh is created using an Afront process.

8. The method of claim 1, wherein the least squares process is weighted.

9. The method of claim 1, comprising smoothing the surface.

10. A system for making an implant from an image of a bone, comprising a processor and a memory, wherein the processor segments desired bone from the image stored in the memory to create a segmentation of desired bone; creates a polygonal mesh from the segmentation of desired bone; extracts a part of the polygonal mesh corresponding to an implant region, parameterizes the part of the polygonal mesh so that every vertex is associated with two parameter values; resamples the polygonal mesh to generate a grid of 3D points spaced in a predetermined distance in parametric domain; and fits a B-spline surface to the grid using a least squares process, wherein the processor minimizes $$F_{smooth}(Q) = \sum_{k=0}^{r} w_k^2 \|S(u_k, v_k) - P_k\|^2 +$$
$$\lambda \sum_{k=0}^{r} (\|S_{uu}(u_k, v_k)\|^2 + \|S_{uv}(u_k, v_k)\|^2 + \|S_{vv}(u_k, v_k)\|^2)$$

where $w_k$ is a weighting coefficient, $S(u_k, v_k)$ is a surface, $P_k$ are sample points, $\lambda$ is a smoothing parameter, and $S_{uu}$, $S_{uv}$ and $S_{vu}$ are the second derivatives of the surface $S(u_k, v_k)$, sends a computer-aided manufacturing (CAM) file based on the B-Spline surface fitted to a manufacturing machine; and the manufacturing machine form the implant based on instructions derived from the CAM file.

11. The system of claim 10, comprising a computer-aided design (CAD) machine that creates a solid CAD model from the B-spline surface.

12. The system of claim 11, comprising adding assembly features to the CAD model.

13. The system of claim 12, wherein the assembly features comprise one or more assembly pins.

14. The system of claim 12, comprising manufacturing the implant using a CAM system based on the CAD model.

15. The system of claim 10, wherein the polygonal mesh is created using a Marching Cubes process.

16. A method for making a patient specific implant, comprising:
   taking an image of at least a portion of a patient's bone;
   a processor receiving the image data of the image of the patient's bone;
   the processor segmenting a desired bone from the image data to create a segmentation of the desired bone;
   the processor creating a polygonal mesh from the segmentation of the desired bone;

the processor extracting a part of the polygonal mesh corresponding to an implant region;

the processor parameterizing the part of the polygonal mesh so that every vertex therein is associated with two parameter values;

the processor resampling the polygonal mesh to generate a grid of 3D points spaced in a predetermined distance in parametric domain;

the processor fitting a B-spline surface to the grid using a least squares process, wherein involves minimizing $$F_{smooth}(Q) = \sum_{k=0}^{r} w_k^2 \|S(u_k, v_k) - P_k\|^2 + \lambda \sum_{k=0}^{r} (\|S_{uu}(u_k, v_k)\|^2 + \|S_{uv}(u_k, v_k)\|^2 + \|S_{vv}(u_k, v_k)\|^2)$$

where $w_k$ is a weighting coefficient, $S(u_k, v_k)$ is a surface, $P_k$ are sample points, $\lambda$ is a smoothing parameter, and $S_{uu}$, $S_{uv}$ and $S_{vu}$ are the second derivatives of the surface $S(u_k, v_k)$;

the processor sending a computer-aided manufacturing (CAM) file based on the B-Spline surface fitted to a manufacturing machine; and the manufacturing machine forming the implant based on instructions derived from the CAM file.

17. The method of claim 16, comprising implanting the patient specific implant in the patient.

18. The method of claim 16, wherein the CAM system manufactures the customized medical implant from a pre-formed implant.

* * * * *